United States Patent
Weiss

(10) Patent No.: US 9,908,925 B2
(45) Date of Patent: Mar. 6, 2018

(54) ULTRA-CONCENTRATED RAPID-ACTING INSULIN ANALOGUE FORMULATIONS

(71) Applicant: CASE WESTERN RESERVE UNIVERSITY, Cleveland, OH (US)

(72) Inventor: Michael A. Weiss, Moreland Hills, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 14/354,667

(22) PCT Filed: Oct. 29, 2012

(86) PCT No.: PCT/US2012/062423
§ 371 (c)(1),
(2) Date: Apr. 28, 2014

(87) PCT Pub. No.: WO2013/063572
PCT Pub. Date: May 2, 2013

(65) Prior Publication Data
US 2014/0323398 A1    Oct. 30, 2014

Related U.S. Application Data

(60) Provisional application No. 61/552,246, filed on Oct. 27, 2011.

(51) Int. Cl.
*C07K 14/62* (2006.01)
*A61K 38/00* (2006.01)

(52) U.S. Cl.
CPC .............. *C07K 14/62* (2013.01); *A61K 38/00* (2013.01)

(58) Field of Classification Search
CPC ................................ A61K 38/00; C07K 14/62
See application file for complete search history.

(56) References Cited

U.S. PATENT DOCUMENTS

| 4,992,418 A | 2/1991 | Katsoyannis et al. |
| 2003/0104981 A1 | 6/2003 | Mandic |
| 2003/0186846 A1 | 10/2003 | Hoeg-Jensen et al. |
| 2006/0069013 A1 * | 3/2006 | Ostergaard et al. ............. 514/4 |
| 2010/0099601 A1 | 4/2010 | Weiss |
| 2010/0298212 A1 | 11/2010 | Miao et al. |
| 2011/0166064 A1 | 7/2011 | Weiss |
| 2011/0257091 A1 | 10/2011 | DiMarchi et al. |

FOREIGN PATENT DOCUMENTS

| JP | 2005-526009 A | 9/2005 |
| JP | 2007-523211 A | 8/2007 |
| JP | 2008-510692 A | 4/2008 |
| WO | 03/048195 A2 | 6/2003 |
| WO | 2005/079860 A | 9/2005 |
| WO | 2006/018450 A2 | 2/2006 |
| WO | WO 2010014946 A2 * | 2/2010 ............. C07K 14/62 |

OTHER PUBLICATIONS

M.A.. Weiss Insulin & Related Proteins-Structure to Function and Pharmacology, Kluwer Academic Publishers, 2002, pp. 103-119.*
Irini Rakatzi, [LysB3, GluB29] insulin: a novel insulin analog with enhanced b-cell protective action, Biochemical and Biophysical Research Communications 310 (2003) 852-859.*
PCT/US12/62423 International Search Report and Written Opinion dated Jan. 31, 2013.

* cited by examiner

*Primary Examiner* — Hasan S Ahmed
*Assistant Examiner* — Erinne R Dabkowski
(74) *Attorney, Agent, or Firm* — Hahn Loeser & Parks LLP

(57) ABSTRACT

A pharmaceutical formulation comprises insulin having a variant insulin B-chain polypeptide containing an ortho-monofluoro-Phenylalanine substitution at position B24 in combination with a substitution of an amino acid containing an acidic side chain at position B10, allowing the insulin to be present at a concentration of between 0.6 mM and 3.0 mM. The formulation may optionally be devoid of zinc. Amino-acid substitutions at one or more of positions B3, B28, and B29 may additionally be present. The variant B-chain polypeptide may be a portion of a proinsulin analog or single-chain insulin analog. The insulin analog may be an analog of a mammalian insulin, such as human insulin. A method of lowering the blood sugar of a patient comprises administering a physiologically effective amount of the insulin analog or a physiologically acceptable salt thereof to the patient.

11 Claims, 9 Drawing Sheets

A

Phe

B

2F-Phe

SEQUENCE LISTING

<160> NUMBER OF SEQ ID NOS: 21

<210> SEQ ID NO 1
<211> LENGTH: 86
<212> TYPE: PRT
<213> ORGANISM: Homo sapiens

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
            85

<210> SEQ ID NO 2
<211> LENGTH: 21
<212> TYPE: PRT
<213> ORGANISM: Homo sapiens

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 3
<211> LENGTH: 30
<212> TYPE: PRT
<213> ORGANISM: Homo sapiens

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: halogenated amino acid
<220> FEATURE:
<221> NAME/KEY: MISC_FEATURE
<222> LOCATION: (3)..(3)
<223> OTHER INFORMATION: X is N or K
<220> FEATURE:
<221> NAME/KEY: MISC_FEATURE
<222> LOCATION: (10)..(10)
<223> OTHER INFORMATION: X is D or E
<220> FEATURE:
<221> NAME/KEY: MISC_FEATURE
<222> LOCATION: (24)..(24)
<223> OTHER INFORMATION: X is Ortho-monofluoro-Phe
<220> FEATURE:
<221> NAME/KEY: MISC_FEATURE
<222> LOCATION: (28)..(28)
<223> OTHER INFORMATION: X is D or P or K
<220> FEATURE:
<221> NAME/KEY: MISC_FEATURE
<222> LOCATION: (29)..(29)
<223> OTHER INFORMATION: X is K or P or A

<400> SEQUENCE: 4

Phe Val Xaa Gln His Leu Cys Gly Ser Xaa Leu Val Glu Ala Leu Tyr
1               5                   10                  15

Leu Val Cys Gly Glu Arg Gly Xaa Phe Tyr Thr Xaa Xaa Thr
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: halogenated amino acid
<220> FEATURE:
<221> NAME/KEY: MISC_FEATURE
<222> LOCATION: (10)..(10)
<223> OTHER INFORMATION: X is D or E
<220> FEATURE:
<221> NAME/KEY: MISC_FEATURE
<222> LOCATION: (24)..(24)
<223> OTHER INFORMATION: X is Ortho-monofluoro-Phe
<220> FEATURE:
<221> NAME/KEY: MISC_FEATURE
<222> LOCATION: (28)..(28)
<223> OTHER INFORMATION: X is D or E or P
<220> FEATURE:
<221> NAME/KEY: MISC_FEATURE
<222> LOCATION: (29)..(29)
<223> OTHER INFORMATION: X is Ornithine or Diaminobutyric acid or
      Diaminoproprionic acid or Norleucine or Aminobutric acid or
      Aminoproprionic acid

<400> SEQUENCE: 5

Phe Val Asn Gln His Leu Cys Gly Ser Xaa Leu Val Glu Ala Leu Tyr
1               5                   10                  15

Leu Val Cys Gly Glu Arg Gly Xaa Phe Tyr Thr Xaa Xaa Thr
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: halogenated amino acid
<220> FEATURE:
<221> NAME/KEY: MISC_FEATURE
<222> LOCATION: (10)..(10)
<223> OTHER INFORMATION: X is D or E
<220> FEATURE:
<221> NAME/KEY: MISC_FEATURE
<222> LOCATION: (24)..(24)
<223> OTHER INFORMATION: X is Ortho-monofluoro-Phe

<400> SEQUENCE: 6

Phe Val Asn Gln His Leu Cys Gly Ser Xaa Leu Val Glu Ala Leu Tyr
1               5                   10                  15

Leu Val Cys Gly Glu Arg Gly Xaa Phe Tyr Thr Lys Pro Thr
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: halogenated amino acid
<220> FEATURE:

```
<221> NAME/KEY: MISC_FEATURE
<222> LOCATION: (10)..(10)
<223> OTHER INFORMATION: X is D or E
<220> FEATURE:
<221> NAME/KEY: MISC_FEATURE
<222> LOCATION: (24)..(24)
<223> OTHER INFORMATION: X is Ortho-monofluoro-Phe

<400> SEQUENCE: 7

Phe Val Asn Gln His Leu Cys Gly Ser Xaa Leu Val Glu Ala Leu Tyr
1               5                   10                  15

Leu Val Cys Gly Glu Arg Gly Xaa Phe Tyr Thr Asp Lys Thr
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: halogenated amino acid
<220> FEATURE:
<221> NAME/KEY: MISC_FEATURE
<222> LOCATION: (10)..(10)
<223> OTHER INFORMATION: X is D or E
<220> FEATURE:
<221> NAME/KEY: MISC_FEATURE
<222> LOCATION: (24)..(24)
<223> OTHER INFORMATION: X is Ortho-monofluoro-Phe

<400> SEQUENCE: 8

Phe Val Lys Gln His Leu Cys Gly Ser Xaa Leu Val Glu Ala Leu Tyr
1               5                   10                  15

Leu Val Cys Gly Glu Arg Gly Xaa Phe Tyr Thr Pro Glu Thr
            20                  25                  30

<210> SEQ ID NO 9
<211> LENGTH: 21
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: X is H or E

<400> SEQUENCE: 9

Gly Ile Val Glu Gln Cys Cys Xaa Ser Ile Cys Ser Leu Tyr Gln Leu
1               5                   10                  15

Glu Asn Tyr Cys Asn
            20

<210> SEQ ID NO 10
<211> LENGTH: 21
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: X is T or H or E

<400> SEQUENCE: 10

Gly Ile Val Glu Gln Cys Cys Xaa Ser Ile Cys Ser Leu Tyr Gln Leu
1               5                   10                  15

Glu Asn Tyr Cys Asn
            20

<210> SEQ ID NO 11
<211> LENGTH: 22
```

```
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: X is H or E

<400> SEQUENCE: 11

Phe Val Asn Gln His Leu Cys Gly Ser Xaa Leu Val Glu Ala Leu Tyr
1               5                   10                  15

Leu Val Cys Gly Glu Arg
            20

<210> SEQ ID NO 12
<211> LENGTH: 8
<212> TYPE: PRT
<213> ORGANISM: Artificial Sequence
<220> FEATURE:
<223> OTHER INFORMATION: halogenated amino acid
<220> FEATURE:
<221> NAME/KEY: MISC_FEATURE
<222> LOCATION: (2)..(2)
<223> OTHER INFORMATION: X is ortho-monofluoro-Phe
<220> FEATURE:
<221> NAME/KEY: MISC_FEATURE
<222> LOCATION: (7)..(7)
<223> OTHER INFORMATION: X is K

<400> SEQUENCE: 12

Gly Xaa Phe Tyr Thr Pro Xaa Thr
1               5

<210> SEQ ID NO 13
<211> LENGTH: 8
<212> TYPE: PRT
<213> ORGANISM: Artificial Sequence
<220> FEATURE:
<223> OTHER INFORMATION: halogenated amino acid
<220> FEATURE:
<221> NAME/KEY: MISC_FEATURE
<222> LOCATION: (2)..(2)
<223> OTHER INFORMATION: X is ortho-monofluoro-Phe
<220> FEATURE:
<221> NAME/KEY: MISC_FEATURE
<222> LOCATION: (7)..(7)
<223> OTHER INFORMATION: X is E

<400> SEQUENCE: 13

Gly Xaa Phe Tyr Thr Pro Xaa Thr
1               5

<210> SEQ ID NO 14
<211> LENGTH: 8
<212> TYPE: PRT
<213> ORGANISM: Artificial Sequence
<220> FEATURE:
<223> OTHER INFORMATION: halogenated amino acid
<220> FEATURE:
<221> NAME/KEY: MISC_FEATURE
<222> LOCATION: (2)..(2)
<223> OTHER INFORMATION: X is ortho-monofluoro-Phe
<220> FEATURE:
<221> NAME/KEY: MISC_FEATURE
<222> LOCATION: (7)..(7)
<223> OTHER INFORMATION: X is Norleucine or Ornithine or Diaminobutyric
      Acid or Diaminopropionic Acid

<400> SEQUENCE: 14

Gly Xaa Phe Tyr Thr Pro Xaa Thr
1               5
```

```
<210> SEQ ID NO 15
<211> LENGTH: 8
<212> TYPE: PRT
<213> ORGANISM: Artificial Sequence
<220> FEATURE:
<223> OTHER INFORMATION: halogenated amino acid
<220> FEATURE:
<221> NAME/KEY: MISC_FEATURE
<222> LOCATION: (2)..(2)
<223> OTHER INFORMATION: X is ortho-monofluoro-Phe
<220> FEATURE:
<221> NAME/KEY: MISC_FEATURE
<222> LOCATION: (6)..(6)
<223> OTHER INFORMATION: X is D or E

<400> SEQUENCE: 15

Gly Xaa Phe Tyr Thr Xaa Pro Thr
1               5

<210> SEQ ID NO 16
<211> LENGTH: 8
<212> TYPE: PRT
<213> ORGANISM: Artificial Sequence
<220> FEATURE:
<223> OTHER INFORMATION: halogenated amino acid
<220> FEATURE:
<221> NAME/KEY: MISC_FEATURE
<222> LOCATION: (2)..(2)
<223> OTHER INFORMATION: X is ortho-monofluoro-Phe
<220> FEATURE:
<221> NAME/KEY: MISC_FEATURE
<222> LOCATION: (7)..(7)
<223> OTHER INFORMATION: X is K

<400> SEQUENCE: 16

Gly Xaa Phe Tyr Thr Asp Xaa Thr
1               5

<210> SEQ ID NO 17
<211> LENGTH: 8
<212> TYPE: PRT
<213> ORGANISM: Artificial Sequence
<220> FEATURE:
<223> OTHER INFORMATION: halogenated amino acid
<220> FEATURE:
<221> NAME/KEY: MISC_FEATURE
<222> LOCATION: (2)..(2)
<223> OTHER INFORMATION: X is ortho-monofluoro-Phe

<400> SEQUENCE: 17

Gly Xaa Phe Tyr Thr Lys Pro Thr
1               5

<210> SEQ ID NO 18
<211> LENGTH: 90
<212> TYPE: DNA
<213> ORGANISM: Artificial Sequence
<220> FEATURE:
<223> OTHER INFORMATION: modified insulin sequence

<400> SEQUENCE: 18
tttgtgaacc aacacctgtg cggctcacac ctggtggaag ctctctacct agtgtgcggg      60
gaacgaggct agttctacac acccaagacc                                      90

<210> SEQ ID NO 19
<211> LENGTH: 90
<212> TYPE: DNA
<213> ORGANISM: Artificial Sequence
<220> FEATURE:
```

```
<223> OTHER INFORMATION: modified insulin sequence

<400> SEQUENCE: 19
tttgttaacc aacatttgtg tggttctcat ttggttgaag ctttgtactt ggtttgtggt        60
gaaagaggtt agttttacac tccaaagact                                         90

<210> SEQ ID NO 20
<211> LENGTH: 261
<212> TYPE: DNA
<213> ORGANISM: Artificial Sequence
<220> FEATURE:
<223> OTHER INFORMATION: modified proinsulin sequence

<400> SEQUENCE: 20
tttgtgaacc aacacctgtg cggctcacac ctggtggaag ctctctacct agtgtgcggg        60
gaacgaggct agttctacac acccaagacc cgccgggagg cagaggacct gcaggtgggg       120
caggtggagc tgggcggcgg ccctggtgca ggcagcctgc agcccttggc cctggagggg       180
tccctgcaga agcgtggcat tgtggaacaa tgctgtacca gcatctgctc cctctaccag       240
ctggagaact actgcaacta g                                                 261

<210> SEQ ID NO 21
<211> LENGTH: 261
<212> TYPE: DNA
<213> ORGANISM: Artificial Sequence
<220> FEATURE:
<223> OTHER INFORMATION: modified proinsulin sequence

<400> SEQUENCE: 21
tttgttaacc aacatttgtg tggttctcat ttggttgaag ctttgtactt ggtttgtggt        60
gaaagaggtt agttttacac tccaaagact agaagagaag ctgaagattt gcaagttggt       120
caagttgaat tgggtggtgg tccaggtgct ggttctttgc aaccattggc tttggaaggt       180
tctttgcaaa agagaggtat tgttgaacaa tgttgtactt ctatttgttc tttgtaccaa       240
ttggaaaact actgtaacta a                                                 261
```

ULTRA-CONCENTRATED RAPID-ACTING INSULIN ANALOGUE FORMULATIONS

CROSS REFERENCE TO RELATED APPLICATIONS

This application claims benefit of pending International Application No. PCT/US12/62423 filed on Oct. 29, 2012 which claims the priority of U.S. Provisional Application No. 61/552,246 filed on Oct. 27, 2012.

STATEMENT REGARDING FEDERALLY SPONSORED RESEARCH OR DEVELOPMENT

This invention was made with government support under grant numbers DK040949 and DK074176 awarded by the National Institutes of Health. The government has certain rights in the invention.

BACKGROUND OF THE INVENTION

This invention relates to polypeptide hormone analogues that exhibit enhanced pharmaceutical properties, such as more rapid pharmacokinetics at polypeptide concentrations greater than are ordinarily employed in pharmaceutical formulations. This invention also relates to insulin analogues that are modified by the incorporation of non-standard amino acids to enable their formulation at concentrations higher than 100 units per ml (U-100) such that (i) rapid-acting pharmacokinetic (PK) and pharmacodynamic (PD) properties are retained relative to wild-type human insulin at a U-100 concentration and such that (ii) their mitogenic properties are not elevated relative to wild-type human insulin. Such non-standard sequences may optionally contain standard amino-acid substitutions at other sites in the A or B chains of an insulin analogue.

The engineering of non-standard proteins, including therapeutic agents and vaccines, may have broad medical and societal benefits. An example of a medical benefit would be optimization of the pharmacokinetic properties of a protein. An example of a further societal benefit would be the engineering of proteins amenable to formulation at high protein concentrations with deterioration of the PK/PD properties of the formulation. An example of a therapeutic protein is provided by insulin. Analogues of insulin containing non-standard amino-acid substitutions may in principle exhibit superior properties with respect to PK/PD or the dependence of PK/PD on the concentration of insulin in the formulation. The challenge posed by the pharmacokinetics of insulin absorption following subcutaneous injection affects the ability of patients with diabetes mellitus (DM) to achieve tight glycemic control and constrains the safety and performance of insulin pumps.

A particular medical need is posed by the marked resistance to insulin exhibited by certain patients with DM associated with obesity, by certain patients with DM associated with a genetic predisposition to insulin resistance, and by patients with DM secondary to lipodystrophy, treatment with corticosteroids, or over-secretion of endogenous corticosteroids (Cushing's Syndrome). The number of patients with marked insulin resistance is growing due to the obesity pandemic in the developed and developing worlds (leading to the syndrome of "diabesity") and due to the increasing recognition of a monogenic form of DM arising from a mutation in mitochondrial DNA in which insulin resistance can be unusually severe (van den Ouweland, J. M., Lemkes, H. H., Ruitenbeek, W., Sandkuijl, L. A., de Vijlder, M. F., Struyvenberg, P. A., van de Kamp, J. J., & Maassen, J. A. (1992) Mutation in mitochondrial tRNA(Leu)(UUR) gene in a large pedigree with maternally transmitted type II diabetes mellitus and deafness. *Nature Genet.* 1, 368-71). Treatment of such otherwise diverse subsets of patients typically requires the subcutaneous injection of large volumes of regular insulin formulations (U-100 strength; ordinarily 0.6 mM insulin or insulin analogue). Injection of such large volumes can lead to pain and variability in the rate of onset and duration of insulin action. Although a U-500 formulation of wild-type insulin is available for clinical use (Humulin® R U-500; Eli Lilly and Co.), the increase in insulin concentration from 0.6 mM to 3 mM leads to a delay in the onset, and prolongation, of insulin action such that the PK/PD properties of Humulin® R U-500, or similar such products, resemble those of a micro-crystalline suspension of protamine-zinc-containing insulin hexamers; this formulation has long been designated neutral protamine Hagadorn (NPH). Prandial use of a U-500 formulation of wild-type insulin by subcutaneous injection would thus be expected to decrease the efficacy of glycemic control and increase the risk of hypoglycemic episodes. Use of Humulin® R U-500, or similar such products in a device for continuous subcutaneous insulin infusion (CSII; an "insulin pump") would likewise be expected to interfere with the ability of the patient or control algorithm to make effective adjustments in insulin infusion rates based on current or past measurements of blood glucose concentrations, leading to suboptimal glycemic control and increased risk of hypoglycemic events.

A well-established principle of insulin pharmacology relates the aggregation state of the injected insulin molecule to the time course of absorption from the depot into capillaries and hence into the systemic circulation. In general the more aggregated are the insulin molecules into high-molecular weight complexes, the greater the delay in absorption and more prolonged the insulin action. Amino-acid substitutions in the insulin molecule that weaken its self-assembly are known in the art to be associated with more rapid absorption relative to wild-type human insulin; examples are provided by the substitution Pro$^{B28}$→Asp (insulin aspart, the active component of Novolog®; Novo-Nordisk, Ltd) and by the paired substitutions Pro$^{B28}$→Lys and Lys$^{B29}$→Pro (insulin Lispro, the active component of Humalog®; Eli Lilly and Co.). Conversely, amino-acid extensions or chemical modifications of the insulin molecule that cause a shift in its isoelectric point (pI) from ca. pH 5 to ca. pH 7 are known in the art to lead to isoelectric precipitation of the modified insulin in the subcutaneous depot; such high molecular-weight complexes provide prolonged absorption as a basal insulin formulation. Examples are provided by NovoSol Basal® (a discontinued product of Novo-Nordisk in which Thr$^{B27}$ was substituted by Arg and in which the C-terminal carboxylate moiety of Thr$^{B30}$ was amidated) and insulin glargine (the active component of Lantus®, a basal formulation in which the B chain was extended by the dipeptide Arg$^{B31}$-Arg$^{B32}$; Sanofi-Aventis, Ltd.). (NovoSol Basal® and Lantus® each contain the additional substitution Asn$^{A21}$→Gly to enable their soluble formulation under acidic conditions (pH 3 and pH 4 respectively) without chemical degradation due to deamidation of Asn$^{A21}$.) Prolongation of classical micro-crystalline insulin suspensions (NPH, semi-lente, lente, and ultra-lente) exhibit a range of intermediate-to-long-acting PK/PD properties reflecting the respective physico-chemical properties of these micro-crystals and their relative rates of dissolution.

The above insulin products, including current and past formulations of wild-type human insulin or animal insulins, employ or employed self-assembly of the insulin molecule as a means to achieve chemical stability, as a means to avoid fibril formation, as a means to modulate PK/PD properties, or as a means to achieve a combination of these objectives. Yet insulin self-assembly can also introduce unfavorable or undesired properties. The non-optimal prolonged PK/PD properties of Humulin® R U-500 (or a similar such product), for example, are likely to be the result of hexamer-hexamer associations in the formulation and in the subcutaneous depot. Indeed, studies of wild-type bovine insulin zinc hexamers in vitro by laser light scattering have provided evidence of progressive hexamer-hexamer interactions in the concentration range 0.3-3 mM. Current and past strategies for the composition of insulin formulations and design of insulin analogues therefore face and have faced an irreconcilable barrier to the development of a rapid-acting ultra-concentrated insulin formulation: whereas self-assembly is necessary to obtain chemical and physical stability, its progressive nature above 0.6 mM leads to unfavorable prolongation of PK/PD.

During the past decade specific chemical modifications to the insulin molecule have been described that selectively modify one or another particular property of the protein to facilitate an application of interest. Whereas at the beginning of the recombinant DNA era (1980) wild-type human insulin was envisaged as being optimal for use in diverse therapeutic contexts, the broad clinical use of insulin analogues in the past decade suggests that a suite of non-standard analogs, each tailored to address a specific unmet need, would provide significant medical and societal benefits. Substitution of one natural amino acid at a specific position in a protein by another natural amino acid is well known in the art and is herein designated a standard substitution. Non-standard substitutions in insulin offer the prospect of accelerated absorption without worsening of PK/PD as a function of insulin analogue concentration in the range 0.6-3.0 mM.

Administration of insulin has long been established as a treatment for diabetes mellitus. Insulin is a small globular protein that plays a central role in metabolism in vertebrates. Insulin contains two chains, an A chain, containing 21 residues, and a B chain containing 30 residues. The hormone is stored in the pancreatic β-cell as a $Zn^{2+}$-stabilized hexamer, but functions as a $Zn^{2+}$-free monomer in the bloodstream. Insulin is the product of a single-chain precursor, proinsulin, in which a connecting region (35 residues) links the C-terminal residue of B chain (residue B30) to the N-terminal residue of the A chain. Crystalline arrays of zinc insulin hexamers within mature storage granules have been visualized by electron microscopy (EM). The sequence of insulin is shown in schematic form in FIG. 1. Individual residues are indicated by the identity of the amino acid (typically using a standard three-letter code), the chain and sequence position (typically as a superscript).

Aromatic side chains in insulin, as in globular proteins in general, may engage in a variety of hydrophobic and weakly polar interactions, involving not only neighboring aromatic rings but also other sources of positive- or negative electrostatic potential. Examples include main-chain carbonyl- and amide groups in peptide bonds. Hydrophobic packing of aromatic side chains is believed to occur within the core of proteins and at non-polar interfaces between proteins. Such aromatic side chains can be conserved among vertebrate proteins, reflecting their key contributions to structure or function. An example of a natural aromatic amino acid is phenylalanine. Its aromatic ring system contains six carbons arranged as a planar hexagon. Aromaticity is a collective property of the binding arrangement among these six carbons, leading to π electronic orbitals above and below the plane of the ring. These faces exhibit a partial negative electrostatic potential whereas the edge of the ring, containing five C—H moieties, exhibits a partial positive electrostatic potential. This asymmetric distribution of partial charges gives rise to a quadrupole electrostatic moment and may participate in weakly polar interactions with other formal or partial charges in a protein. An additional characteristic feature of an aromatic side chains is its volume. Determinants of this volume include the topographic contours of its five C—H moieties at the edges of the planar ring. Substitution of one C—H moiety by a C—F moiety would be expected to preserve its aromaticity but introduced a significant dipole moment in the ring due to the electronegativity of the fluorine atom and consequent distortion of the π electronic orbitals above and below the plane of the ring. Whereas the size of the C—F moiety is similar to that of the native C—H moiety (and so could in principle be accommodated in diverse protein environments), its local electronegativity and ring-specific fluorine-induced electrostatic dipole moment could introduce favorable or unfavorable electrostatic interactions with neighboring groups in a protein. Examples of such neighboring groups include, but are not restricted to, CO—NH peptide bond units, lone pair electrons of sulfur atoms in disulfide bridges, side-chain carboxamide functions (Asn and Gln), other aromatic rings (Phe, Tyr, Trp, and His), and the formal positive and negative charges of acidic side chains (Asp and Glu), basic side chains (Lys and Arg), a titratable side chain with potential $pK_a$ in the range used in insulin formations (His), titratable N- and C-terminal chain termini, bound metal ions (such as $Zn^{2+}$ or $Ca^{2+}$), and protein-bound water molecules.

An example of a conserved aromatic residue in a therapeutic protein is provided by phenylalanine at position B24 of the B chain of insulin (designated $Phe^{B24}$). This is one of three phenylalanine residues in insulin (positions B1, B24, and B25). A structurally similar tyrosine is at position B26. The structural environment of $Phe^{B24}$ in an insulin monomer is shown in a ribbon model (FIG. 2A) and in a space-filling model (FIG. 2B). Conserved among vertebrate insulins and insulin-like growth factors, the aromatic ring of $Phe^{B24}$ packs against (but not within) the hydrophobic core to stabilize the super-secondary structure of the B chain. $Phe^{B24}$ lies at the classical receptor-binding surface and has been proposed to direct a change in conformation on receptor binding. $Phe^{B24}$ packs at the dimer interface of insulin and so at three interfaces of an insulin hexamer. Its structural environment in the insulin monomer differs from its structural environment at these interfaces. In particular, the surrounding volume available to the side chain of $Phe^{B24}$ is larger in the monomer than in the dimer or hexamer.

A major goal of insulin replacement therapy in patients with DM is tight control of the blood glucose concentration to prevent its excursion above or below the normal range characteristic of healthy human subjects. Excursions below the normal range are associated with immediate adrenergic or neuroglycopenic symptoms, which in severe episodes lead to convulsions, coma, and death. Excursions above the normal range are associated with increased long-term risk of microvascular disease, including retinaphthy, blindness, and renal failure. Because the pharmacokinetics of absorption of wild-type human insulin or human insulin analogues—when formulated at strengths greater than U-100—is often too slow, too prolonged and too variable relative to the physiological requirements of post-prandial metabolic homeostasis, patients with DM associated with marked insulin resistance often fail to achieve optimal glycemic targets and are thus at increased risk of both immediate and long-term complications. Thus, the safety, efficacy, and real-world convenience of regular and rapid-acting insulin products have been limited by prolongation of PK/PD as the concentration of self-assembled insulin or insulin analogue is made higher than ca. 0.6 mM.

The present invention circumvents the necessity for insulin self-assembly as a mechanism to achieve a formulation of sufficient chemical stability and of sufficient physical stability to meet or exceed regulatory standards. Chemical degradation refers to changes in the arrangement of atoms in the insulin molecule, such as deamidation of Asn, formation of iso-Asp, and breakage of disulfide bridges. The susceptibility of insulin to chemical degradation is correlated with its thermodynamic stability (as probed by chemical denaturation experiments); because it is the monomer that is the species most susceptible to chemical degradation, its rate is reduced by sequestration of monomers within self-assemblies. Physical degradation refers to fibril formation (fibrillation), which is a non-native form of self-assembly that leads to linear structures containing thousands (or more) of insulin protomers in a beta-sheet rich conformation. Fibrillation is a serious concern in the manufacture, storage and use of insulin and insulin analogues above room temperature. Rates of fibrillation are enhanced with higher temperature, lower pH, agitation, or the presence of urea, guanidine, ethanol co-solvent, or hydrophobic surfaces. Current US drug regulations demand that insulin be discarded if fibrillation occurs at a level of one percent or more. Because fibrillation is enhanced at higher temperatures, patients with DM optimally must keep insulin refrigerated prior to use. Fibrillation of insulin or an insulin analogue can be a particular concern for such patients utilizing an external insulin pump, in which small amounts of insulin or insulin analogue are injected into the patient's body at regular intervals. In such a usage, the insulin or insulin analogue is not kept refrigerated within the pump apparatus, and fibrillation of insulin can result in blockage of the catheter used to inject insulin or insulin analogue into the body, potentially resulting in unpredictable fluctuations in blood glucose levels or even dangerous hyperglycemia. At least one recent report has indicated that insulin Lispro (KP-insulin, an analogue in which residues B28 and B29 are interchanged relative to their positions in wild-type human insulin; trade name Humalog®) may be particularly susceptible to fibrillation and resulting obstruction of insulin pump catheters. Insulin exhibits an increase in degradation rate of 10-fold or more for each 10° C. increment in temperature above 25° C.; accordingly, guidelines call for storage at temperatures <30° C. and preferably with refrigeration. Such formulations typically include a predominance of native insulin self-assemblies.

The present theory of protein fibrillation posits that the mechanism of fibrillation proceeds via a partially folded intermediate state, which in turn aggregates to form an amyloidogenic nucleus. In this theory, it is possible that amino-acid substitutions that stabilize the native state may or may not stabilize the partially folded intermediate state and may or may not increase (or decrease) the free-energy barrier between the native state and the intermediate state. Therefore, the current theory indicates that the tendency of a given amino-acid substitution in the insulin molecule to increase or decrease the risk of fibrillation is highly unpredictable; in particular the lag time observed prior to onset of detectable fibrillation does not correlate with measurements of the thermodynamic stability of the native-state monomer (as probed by chemical denaturation experiments). Whereas a given substitution may stabilize both the overall native state and amyloidogenic partial fold—and so delay the onset of fibrillation—another substitution may stabilize the native state but not the amyloidogenic partial fold and so have little or no effect on the lag time. Still other substitutions may destabilize the native state but stabilize the amyloidogenic partial fold, and so lead to accelerated fibrillation despite its apparent stabilizing properties.

There is a need, therefore for an insulin analogue that displays rapid PK/PD for the treatment of DM under a broad range of insulin concentrations from 0.6 mM to 3.0 mM (typically corresponding to formulation strengths in a range from U-100 to U-500) while exhibiting at least a portion of the activity of the corresponding wild-type insulin, maintaining at least a portion of its chemical and/or physical stability.

SUMMARY OF THE INVENTION

It is an aspect of the present invention to provide insulin analogues that provide zinc-free monomeric and dimeric species of sufficient chemical stability and physical stability to enable their formulation at a range of protein concentrations and in a form that confers rapid absorption following subcutaneous injection. The present invention addresses previous limitations for ultra-concentrated insulin formulations and insulin analogues formulations, namely, that they still do not act sufficiently quickly to optimize post-prandial glycemic control or enable use in insulin pumps. The claimed invention circumvents previous design restrictions, including those regarding substitution of $Phe^{B24}$, through the incorporation of a non-standard amino-acid substitution at position B24. The non-standard amino-acid side chain (2F-$Phe^{B24}$; also designated ortho-monofluoro-$Phe^{B24}$) at position B24 markedly stabilizes the isolated insulin monomer. This is achieved by substitution of an aromatic amino-acid side chain by a halogen-modified aromatic analogue, similar in size and shape to Phenylalanine, where the analogue then maintains at least a portion of biological activity of the corresponding insulin or insulin analogue containing the native aromatic side chain. Further, the modified side chain reduces the cross-binding of insulin to the Type-I IGF receptor (IGF-IR) and modulates binding to the insulin receptor such that the aberrant mitogenic properties conferred by the stabilizing substitution $His^{B10} \rightarrow Asp$ are circumvented. It is another aspect of the present invention that the 2-F-$Phe^{B24}$ modification is combined with an acidic side chain at position B10 (Asp or Glu) such that the resulting analogue has an affinity for IGF-IR similar to that of wild-type human insulin. It is another aspect of the present invention that such an insulin analogue may be formulated in at pH 7-8 at strengths from U-100 to U-500 (approximately 0.6-3.0 mM), optionally in zinc-free formulations, with preservation of PK/PD properties similar to, or more rapid and less prolonged than, those of regular formulations of wild-type human insulin at strength U-100. In one particular embodiment, the concentration of insulin in the formulation is at least 2 mM. It is yet another aspect of the present invention that the insulin analogue containing 2F-$Phe^{B24}$ and an acidic side chain at position B10 may contain additional substitutions in the A chain or B chain that further enhance chemical or physical stability or that further impair self-assembly.

In general, the present invention provides a pharmaceutical formulation comprising insulin having a variant insulin B-chain polypeptide containing an ortho-monofluoro-Phenylalanine substitution at position B24 in relation to the sequence of human insulin, in combination with a substitution of an amino acid containing an acidic side chain at position B10 in relation to the sequence of human insulin selected from Aspartic Acid and Glutamic Acid, wherein the insulin is present at a concentration of between 0.6 mM and 3.0 mM. In some particular embodiments the pharmaceutical formulation contains insulin at a concentration of at least 2 mM. In one particular embodiment, the pharmaceutical formulation contains insulin at a concentration of 2.4 mM or more.

In addition or in the alternative, the insulin analogue may be a mammalian insulin analogue, such as an analogue of human insulin. In one set of embodiments, the B-chain polypeptide comprises an amino-acid sequence selected from the group consisting of SEQ. ID. NOS. 4-7 and polypeptides having three or fewer additional amino-acid substitutions thereof. In still another embodiment, the A chain contains a substitution at position A8 (SEQ. ID, NO. 8 in addition to B-chain modifications) selected from the group consisting of SEQ. ID. NOS. 4-7.

In another embodiment, the insulin analogue may optionally contain a non-standard amino-acid substitution at position 29 of the B chain. In one example, the non-standard amino acid at B29 is norleucine (Nle). In another example, the non-standard amino acid at B29 is ornithine (Orn). In still other examples, the non-standard amino acid may be Aminobutyric acid, Aminopropionic acid, Diaminobutyric acid, or Diaminopropionic acid.

Also provided is a nucleic acid encoding an insulin analogue comprising a B-chain polypeptide that incorporates a non-standard amino acid at position B24. In one example, the non-standard amino acid is encoded by a stop codon, such as the nucleic acid sequence TAG. An expression vector may comprise such a nucleic acid and a host cell may contain such an expression vector.

The invention also provides a method of lowering the blood sugar level of a patient. The method comprises administering a physiologically effective amount of an insulin analogue or a physiologically acceptable salt thereof to the patient, wherein the insulin analogue or a physiologically acceptable salt thereof contains a B-chain polypeptide incorporating an ortho-monofluoro-Phenylalanine (2F-Phe) at position B24 and an Asp or Glu substitution at position B10. In still another embodiment, the insulin analogue is a mammalian insulin analogue, such as an analogue of human insulin. In some embodiments, the B-chain polypeptide comprises an amino-acid sequence selected from the group consisting of SEQ. ID. NOS. 4-7 and polypeptides having three or fewer additional amino-acid substitutions thereof. In other embodiments, the A-chain polypeptide comprises an amino-acid sequence selected from the group consisting of SEQ. ID. NOS. 8 in combination with a B-chain polypeptide comprising an amino-acid sequence selected from the group consisting of SEQ. ID. NOS. 4-7.

It is a further aspect of the present invention to provide a polypeptide comprising a variant insulin B-chain polypeptide sequence containing an ortho-monofluoro-Phenylalanine substitution at position B24 in relation to the sequence of human insulin, in combination with a substitution of an amino acid containing an acidic side chain at position B10 in relation to the sequence of human insulin, and a substitution of a non-standard amino acid at position B29 in relation to the sequence of human insulin selected from the group consisting of Ornithine, Diaminobutyric acid, Diaminopropionic acid, Norleucine, Aminobutyric acid, and Aminopropionic acid. In some embodiments, the polypeptide may be a proinsulin analogue or single-chain insulin analogue.

DETAILED DESCRIPTION OF THE INVENTION

Figure 1:
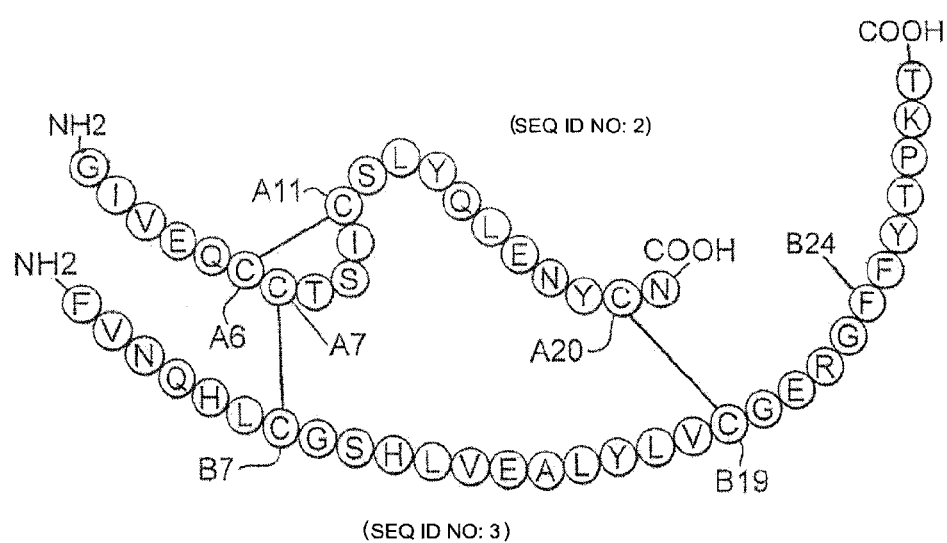
FIG. 1 a schematic representation of the sequence of human insulin indicating the position of residue B24 in the B chain.

The present invention is directed an insulin analogue that enables rapid PK and PD to be maintained at a broad range of insulin concentrations from U-100 to U-500. The analogue then maintains at least a portion of biological activity of the corresponding unmodified insulin or insulin analogue and maintains similar or enhanced thermodynamic stability and resistance to fibril formation. We have invented an insulin analogue with PK/PD properties similar to or more rapid than regulation formulations of wild-type human insulin at U-100 strength (e.g., Humulin R® U-100; Eli Lilly and Co.) such that these PK/PD properties are not significantly affected by the concentration of insulin analogue in the range 0.6 mM-3.0 mM.

The present invention pertains to a non-standard fluorous modification at position B24 to improve the properties of ultra-concentrated insulin formulations with respect to rapidity of absorption following subcutaneous injection. In one instance the insulin analogue is an engineered dimer that contains acidic substitutions (Glu or Asp) at position B10, introduced to prevent binding of zinc ions by native residue His$^{B10}$ and to destabilize the trimer interface of insulin as defined in molecular structures of zinc insulin hexamers. In another instance, the analogue is an engineered monomer that contains, in addition to the acidic substitutions at position B10 described above, additional substitutions at positions B28 and/or B29, introduced to destabilize the classical dimer interface of insulin as defined in molecular structures of zinc insulin hexamers and zinc-free dimers. In yet another instance the dimeric and monomeric analogues described above may contain an additional substitution at position A8.

In either of two particular embodiments (2F-Phe$^{B24}$-DKP-insulin (where DKP represents Asp$^{B10}$, Lys$^{B28}$ and Pro$^{B29}$), and 2F-Phe$^{B24}$-[Asp$^{B10}$, Orn$^{B29}$]-insulin; where Orn designates ornithine) the present invention provides an insulin analogue that exhibits an affinity for the Type I IGF receptor similar to or lower than that of wild-type human insulin, an activity in stimulating the autophosphorylation of the Type I IGF receptor that is similar to or lower than that of wild-type human insulin, and an activity in stimulating the proliferation of a human breast-cancer-derived cell line that is similar to or lower than that of wild-type human insulin. The present invention is not limited, however, to 2F-Phe$^{B24}$-derivatives of human insulin and its analogues. It is also envisioned that these substitutions may also be made in dimeric and monomeric analogues derived from animal insulins such as porcine, bovine, equine, and canine insulins, by way of non-limiting examples.

It has been discovered that 2F-Phe$^{B24}$-DKP insulin and 2F-Phe$^{B24}$-[Asp$^{B10}$, Orn$^{B29}$]-insulin, when formulated in Lilly Diluent and following subcutaneous injection in a male Lewis rat rendered diabetic by streptozotocin, will direct a reduction in blood glucose concentration with a potency similar to that of wild-type human insulin in the same formulation. It has also been discovered that 2F-Phe$^{B24}$-DKP-insulin and 2F-Phe$^{B24}$-[Asp$^{B10}$, Orn$^{B29}$]-insulin, when formulated in Lilly Diluent and following subcutaneous injection in an anesthetized Yorkshire pig whose endogenous b-cell secretion of insulin was suppressed by intravenous administration of octreotide, will direct a reduction in blood glucose concentration with a potency similar to that of wild-type human insulin in the same formulation.

In addition or in the alternative, the insulin analogue of the present invention may contain a standard or non-standard amino-acid substitution at position 29 of the B chain, which is lysine (Lys) in wild-type insulin. In one example, the non-standard amino acid at B29 is norleucine (Nle). In another example, the non-standard amino acid at B29 is ornithine (Orn).

Furthermore, in view of the similarity between human and animal insulins, and use in the past of animal insulins in human patients with diabetes mellitus, it is also envisioned that other minor modifications in the sequence of insulin may be introduced, especially those substitutions considered "conservative." For example, additional substitutions of amino acids may be made within groups of amino acids with similar side chains, without departing from the present invention. These include the neutral hydrophobic amino acids: Alanine (Ala or A), Valine (Val or V), Leucine (Leu or L), Isoleucine (Ile or I), Proline (Pro or P), Tryptophan (Trp or W), Phenylalanine (Phe or F) and Methionine (Met or M). Likewise, the neutral polar amino acids may be substituted for each other within their group of Glycine (Gly or G), Serine (Ser or S), Threonine (Thr or T), Tyrosine (Tyr or Y), Cysteine (Cys or C), Glutamine (Glu or Q), and Asparagine (Asn or N). Basic amino acids are considered to include Lysine (Lys or K), Arginine (Arg or R) and Histidine (His or H). Acidic amino acids are Aspartic acid (Asp or D) and Glutamic acid (Glu or E). Unless noted otherwise or wherever obvious from the context, the amino acids noted herein should be considered to be L-amino acids. Standard amino acids may also be substituted by non-standard amino acids belong to the same chemical class. By way of non-limiting example, the basic side chain Lys may be replaced by basic amino acids of shorter side-chain length (Ornithine, Diaminobutyric acid, or Diaminopropionic acid). Lys may also be replaced by the neutral aliphatic isostere Norleucine (Nle), which may in turn be substituted by analogues containing shorter aliphatic side chains (Aminobutyric acid or Aminopropionic acid).

In one example, the insulin analogue of the present invention contains four or fewer conservative substitutions other than the 2F-Phe$^{B24}$ and B10 substitutions of the present invention. In a pair of particular examples, the formulation containing a variant B-chain polypeptide sequence also contains an Asn or Lys substitution at position B3 relative to human insulin. In addition or in the alternative, the formulation may additionally include an insulin A-chain polypeptide sequence containing a Glutamic acid substitution or a Histidine substitution at position A8.

Figure 3A:
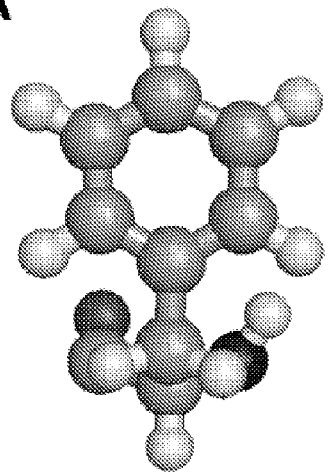
FIG. 3A is a series of ball and stick (top) and space-filling (bottom) representations of phenylalanine (Phe).
Figure 3A:
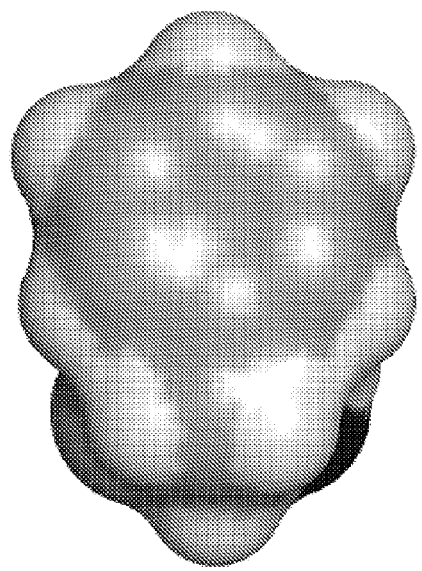
Figure 3B:
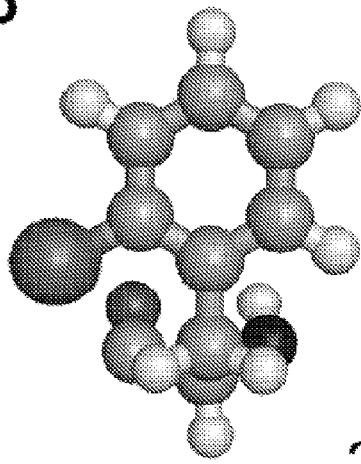
FIG. 3B is a series of ball and stick (top) and space-filling (bottom) representations of 2F-Phe.
Figure 3B:
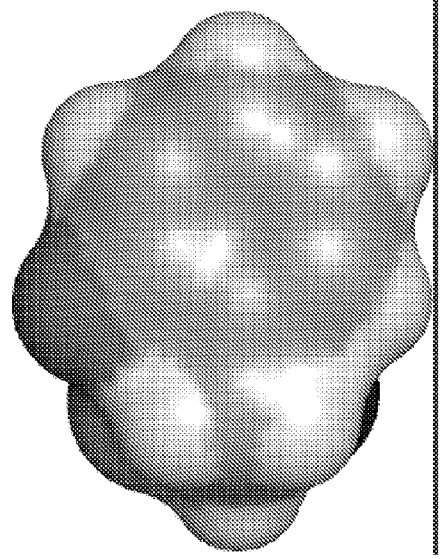

As used in this specification and the claims, various amino acids in insulin or an insulin analogue may be noted by the amino-acid residue in question, followed by the position of the amino acid, optionally in superscript. The position of the amino acid in question includes the A- or B chain of insulin where the substitution is located. Thus, $Phe^{B24}$ denotes a phenylalanine at the twenty-fourth amino acid of the B chain of insulin. Fluoro-derivatives of aromatic rings retain planarity, but differ in distribution of π electrons leading to changes in electrostatic potential as illustrated in front and side views of Phenylalanine (FIG. 3A) relative to 2F-Phenylalanine (FIG. 3B). As used herein, the recited position of a particular substitution should be understood to be the position relative to wild type human insulin, regardless of the particular species being used in any particular embodiment under discussion. In this way, the location of a substitution will be identifiable regardless of any insertions, extensions or deletions in a particular polypeptide.

The present invention envisions that 2F modification at $Phe^{B24}$ introduces an electronegative atom and electrostatic dipole moment that result in (i) thermodynamic stabilization of the insulin monomer and (ii) an alteration in the functional character of the receptor-binding surface. Whereas there are substitutions known in the art that enhance the stability of insulin in concern with augmentation of receptor binding, 2F-$Phe^{B24}$ stabilizes insulin while decreasing receptor binding. In particular, this alteration serves to counteract the effects of acidic substitutions at position B10 (Asp or Glu) to enhance binding to, and signaling through, the Type I IGF receptor; this alteration serves to counteract the effects of such B10 substitutions to enhance binding to the insulin receptor, presumably by reducing the residence time of the analogue on the receptor; and by means of these and other possible mechanisms, 2F-$Phe^{B24}$ enables the incorporation of acidic residues at B10 without incurring excess mitogenicity relative to wild-type human insulin.

Figure 2A:
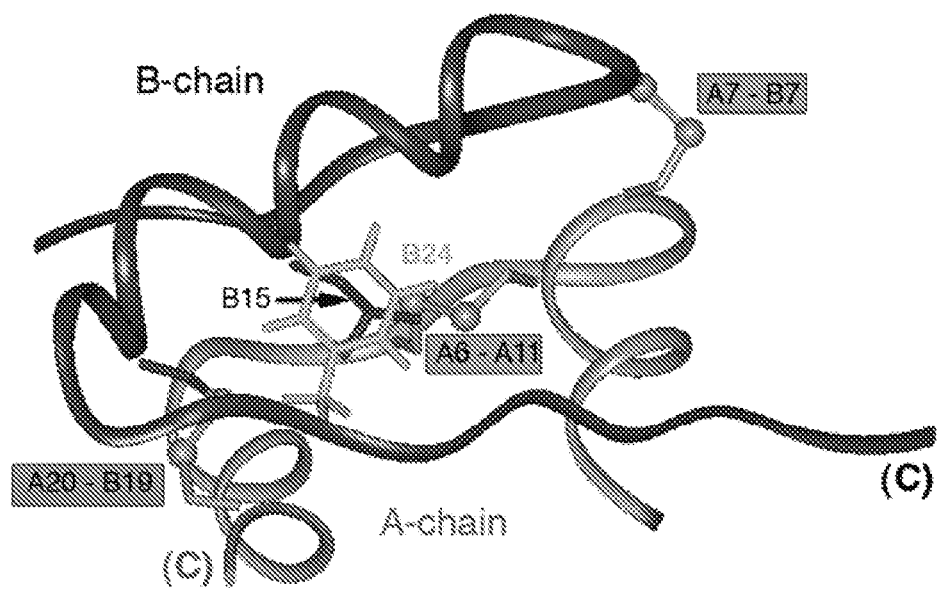
FIG. 2A is a ribbon model of an insulin monomer showing aromatic residue of $Phe^{B24}$ in relation to the three disulfide bridges. The adjoining side chains of $Leu^{B15}$ (arrow) and $Phe^{B24}$ are shown. The A- and B chains are otherwise shown in light and dark gray, respectively, and the sulfur atoms of cysteines as circles.
Figure 2B:
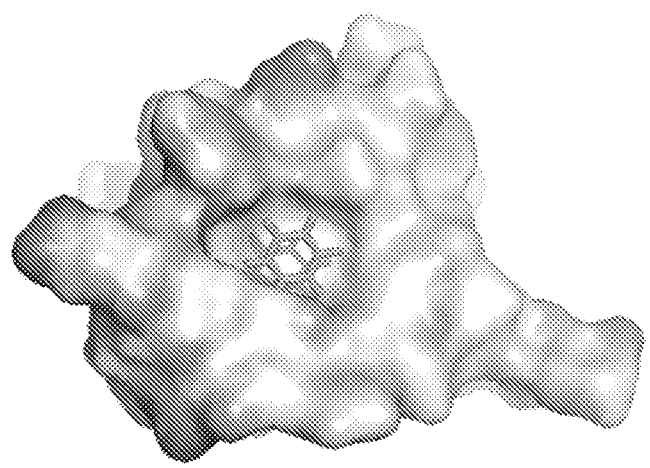
FIG. 2B is a space-filling model of insulin showing the $Phe^{B24}$ side chain within a pocket at the edge of the hydrophobic core.

The phenylalanine at B24 is an invariant amino acid in functional insulin and contains an aromatic side chain. The biological importance of $Phe^{B24}$ in insulin is indicated by a clinical mutation ($Ser^{B24}$) causing human diabetes mellitus. While not wishing to be bound by theory, $Phe^{B24}$ is believed to pack at the edge of a hydrophobic core at the classical receptor binding surface. The models are based on a crystallographic protomer (2-Zn molecule 1; Protein Databank identifier 4INS). Lying within the C-terminal β-strand of the B chain (residues B24-B28), $Phe^{B24}$ adjoins the central α-helix (residues B9-B19) (FIG. 2A). In the insulin monomer one face and edge of the aromatic ring sit within a shallow pocket defined by $Leu^{B15}$ and $Cys^{B19}$; the other face and edge are exposed to solvent (FIG. 2B). This pocket is in part surrounded by main-chain carbonyl and amide groups and so creates a complex and asymmetric electrostatic environment with irregular and loose steric borders. In the insulin dimer, and within each of the three dimer interfaces of the insulin hexamer, the side chain of $Phe^{B24}$ packs within a more tightly contained spatial environment as part of a cluster of eight aromatic rings per dimer interface ($Tyr^{B16}$, $Phe^{B24}$, $Phe^{B25}$, $Tyr^{B26}$ and their dimer-related mates). Irrespective of theory, substitution of the aromatic ring of $Phe^{B24}$ by a 2F derivative preserves general hydrophobic packing within the dimer interface while introducing favorable asymmetric electrostatic interactions within the insulin monomer.

The present invention pertains to a non-standard modification at position B24 to improve the properties of ultra-concentrated formulations of dimeric or monomeric insulin analogues with respect to physical stability, chemical stability, and mitogenicity. Because of these improvements, the insulin analogues can be formulated at strengths greater than U-100 and up to U-500 such that, irrespective of the concentration of insulin analogue, the formulation maintains a rapidity of absorption and pharmacologic activity following subcutaneous injection similar to that of a regular wild-type human insulin U-100 formulation; examples of the latter are Humulin® R U-100 (Eli Lilly and Co) or Novalin® R U-100 (Novo-Nordisk). In one instance the insulin analogue contains 2F-$Phe^{B24}$ in association with an acidic substitution (Asp or Glu) at position B10. In yet other instances the non-standard amino-acid substitution at B24 is accompanied both by an acidic substitution at B10 and by a non-standard substitution at position B29 or by three or fewer standard substitutions elsewhere in the A- or B chains.

It is envisioned that the substitutions of the present invention may be made in any of a number of existing insulin analogues. For example, the ortho-fluoro derivative of Phenylalanine at position B24 (2F-$Phe^{B24}$) provided herein may be made in insulin analogues that contain an acidic residue at position B10 in the context of insulin Lispro ([$Lys^{B28}$, $Pro^{B29}$]-insulin, herein abbreviated KP-insulin), insulin Aspart ($Asp^{B28}$-insulin), insulin Glulisine ([$Lys^{B3}$, $Glu^{B29}$]-insulin), or other modified insulins or insulin analogues, or within various pharmaceutical formulations, such as regular insulin, NPH insulin, lente insulin or ultralente insulin, in addition to human insulin. Insulin Aspart contains an $Asp^{B28}$ substitution and is sold as Novalog® whereas insulin Lispro contains $Lys^{B28}$ and $Pro^{B29}$ substitutions and is known as and sold under the name Humalog®; insulin Glulisine contains substitutions $Lys^{B28}$ and $Pro^{B29}$ and is known as and sold under the name Apidra®. These analogues are described in U.S. Pat. Nos. 5,149,777, 5,474,978, and 7,452,860. These analogues are each known as fast-acting insulins.

The amino-acid sequence of human proinsulin is provided, for comparative purposes, as SEQ ID NO: 1.

(human proinsulin)
SEQ ID NO: 1
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr-Arg-Arg-Glu-Ala-Glu-Asp- Leu-Gln-Val-Gly-Gln-Val-Glu-Leu-Gly-Gly-Gly-Pro- Gly-Ala-Gly-Ser-Leu-Gln-Pro-Leu-Ala-Leu-Glu-Gly- Ser-Leu-Gln-Lys-Arg-Gly-Ile-Val-Glu-Gln-Cys-Cys- Thr-Ser-Ile-Cys-Ser-Leu-Tyr-Gln-Leu-Glu-Asn-Tyr- Cys-Asn The amino-acid sequence of the A chain of human insulin is provided as SEQ ID NO: 2.

(human A chain)
SEQ ID NO: 2
Gly-Ile-Val-Glu-Gln-Cys-Cys-Thr-Ser-Ile-Cys-Ser-

Leu-Tyr-Gln-Leu-Glu-Asn-Tyr-Cys-Asn

The amino-acid sequence of the B chain of human insulin is provided as SEQ ID NO: 3.

(human B chain)

SEQ ID NO: 3

Phe-Val-Asn-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-Lys-Thr

The amino-acid sequence of a B chain of human insulin may be modified with a substitution of a ortho-monofluoro-Phenylalanine (2F-Phe) at position B24. An example of such a sequence is provided as SEQ. ID. NO 4.

SEQ ID NO: 4

Phe-Val-Xaa$_5$-Gln-His-Leu-Cys-Gly-Ser-Xaa$_4$-Leu-Val-

Glu-Ala-Leu-Tyr-Leu-Val-Cys-Gly-Glu-Arg-Gly-Xaa$_1$-

Phe-Try-Thr-Xaa$_2$-Xaa$_3$-Thr

[Xaa$_1$ is 2F-Phe; Xaa$_2$ is Asp, Pro, Lys, or Arg; Xaa$_3$ is Lys, Pro, or Ala; Xaa$_4$ is Asp or Glu; and Xaa$_5$ is Asn or Lys]

Substitution of a 2F-Phe at position B24 may optionally be combined with non-standard substitutions at position B29 as provided in SEQ. ID. NO 5.

SEQ ID NO: 5

Phe-Val-Asn-Gln-His-Leu-Cys-Gly-Ser-Xaa$_4$-Leu-Val-

Glu-Ala-Leu-Tyr-Leu-Val-Cys-Gly-Glu-Arg-Gly-Xaa$_1$-

Phe-Try-Thr-Xaa$_2$-Xaa$_3$-Thr

[Xaa$_1$ is 2F-Phe; Xaa$_2$ is Asp, Glu, or Pro; Xaa$_3$ is Ornithine, Diaminobutyric acid, Diaminoproprionic acid, Norleucine, Aminobutric acid, or Aminoproprionic acid; and Xaa$_4$ is Asp or Glu]

Further combinations of other substitutions are also within the scope of the present invention. It is also envisioned that the substitutions and/or additions of the present invention may also be combined with substitutions of prior known insulin analogues. For example, the amino-acid sequence of an analogue of the B chain of human insulin containing the Lys$^{B28}$ and Pro$^{B29}$ substitutions of insulin Lispro, in which the 2F-Phe$^{B24}$ substitution may also be introduced, is provided as SEQ ID NO: 6.

SEQ ID NO: 6

Phe-Val-Asn-Gln-His-Leu-Cys-Gly-Ser-Xaa$_2$-Leu-Val-

Glu-Ala-Leu-Tyr-Leu-Val-Cys-Gly-Glu-Arg-Gly-Xaa$_1$-

Phe-Tyr-Thr-Lys-Pro-Thr

[Xaa$_1$ is 2F-Phe, and Xaa$_2$ is Asp or Glu]

Similarly, the amino-acid sequence of an analogue of the B chain of human insulin containing the Asp$^{B28}$ substitution of insulin Aspart, in which the 2F-Phe$^{B24}$ substitution may also be introduced, is provided as SEQ ID NO: 7.

SEQ ID NO: 7

Phe-Val-Asn-Gln-His-Leu-Cys-Gly-Ser-Xaa$_2$-Leu-Val-

Glu-Ala-Leu-Tyr-Leu-Val-Cys-Gly-Glu-Arg-Gly-Xaa$_1$-

Phe-Tyr-Thr-<u>Asp</u>-Lys-Thr.

[Xaa$_1$ is 2F-Phe, and Xaa$_2$ is Asp or Glu]

In still another embodiment, the B-chain insulin analogue polypeptide contains a Lysine at position B3, Glutamic acid at position B29, and ortho-monofluoro-Phenylalanine at position B24 as provided as SEQ ID NO: 8.

SEQ ID NO: 8

Phe-Val-<u>Lys</u>-Gln-His-Leu-Cys-Gly-Ser-Xaa$_2$-Leu-Val-

Glu-Ala-Leu-Tyr-Leu-Val-Cys-Gly-Glu-Arg-Gly-Xaa$_1$-

Phe-Tyr-Thr-Pro-<u>Glu</u>-Thr.

[Xaa$_1$ is 2F-Phe, and Xaa$_2$ is Asp or Glu]

A 2F-Phe$^{B24}$ substitution may also be introduced in combination with other insulin analogue substitutions such as analogues of human insulin containing a substitution at residue A8 as described more fully in co-pending International Application No. PCT/US07/00320 and U.S. application Ser. No. 12/160,187. For example, the 2F-Phe$^{B24}$ substitution may be present with His$^{A8}$ or Glu$^{A8}$ in which the variant A chain is provided in SEQ ID NO: 9,

SEQ ID NO: 9

Gly-Ile-Val-Glu-Gln-Cys-Cys-Xaa$_1$-Ser-Ile-Cys-Ser-

Leu-Tyr-Gln-Leu-Glu-Asn-Tyr-Cys-Asn;

wherein Xaa$_1$ is His or Glu.

The insulin analogues provided in SEQ ID NO: 4-8 may be prepared by trypsin-catalyzed semi-synthesis in which a des-octapeptide[B23-B30] fragment of Asp$^{B10}$-insulin, Glu$^{B10}$-insulin, or variants thereof containing an additional substitution at position A8, is employed as provided in SEQ ID NOS: 10 and 11 wherein the A and B chain are connected by cystines A7-B7 and A20-B19 and wherein the A chain contains cystine A6-A11.

(A chain)

SEQ ID NO: 10

Gly-Ile-Val-Glu-Gln-Cys-Cys-Xaa-Ser-Ile-Cys-Ser-

Leu-Tyr-Gln-Leu-Glu-Asn-Tyr-Cys-Asn wherein Xaa is Thr, His, or Glu (B chain)

SEQ ID NO: 11

Phe-Val-Asn-Gln-His-Leu-Cys-Gly-Ser-Xaa-Leu-Val-

Glu-Ala-Leu-Tyr-Leu-Val-Cys-Gly-Glu-Arg wherein Xaa is His or Glu.

Trypsin-mediated semisynthesis also employs a synthetic octapeptide containing ortho-monofluoro-Phenylalanine (2F-Phe) as provided in SEQ ID NOS: 12-14.

SEQ ID NO: 12

Gly-Xaa$_1$-Phe-Tyr-Thr-Pro-Xaa$_2$-Thr.

[Xaa$_1$ is 2F-Phe and Xaa$_2$ is Lys containing a removable protecting group attached to its ε-amino function]

SEQ ID NO: 13

Gly-Xaa$_1$-Phe-Tyr-Thr-Pro-Xaa$_2$-Thr.

[Xaa$_1$ is 2F-Phe and Xaa$_2$ is Glu]

SEQ ID NO: 14
Gly-Xaa₁-Phe-Tyr-Thr-Pro-Xaa₂-Thr.

[Xaa₁ is 2F-Phe and Xaa₂ is Norleucine, Ornithine, Diaminobutyric Acid, or Diaminopropionic Acid]

SEQ ID NO: 15
Gly-Xaa₁-Phe-Tyr-Thr-Xaa2-Pro-Thr.

[Xaa₁ is 2F-Phe and Xaa₂ is Asp or Glu]

SEQ ID NO: 16
Gly-Xaa₁-Phe-Tyr-Thr-<u>Asp</u>-Xaa₂-Thr.

[Xaa₁ is 2F-Phe and Xaa₂ is Lys containing a removable protecting group attached to its ε-amino function]

SEQ ID NO: 17
Gly-Xaa₁-Phe-Tyr-Thr-<u>Lys</u>-<u>Pro</u>-Thr.

[Xaa₁ is 2F-Phe]

An ortho-monofluoro-Phenylalanine substitution at B24 may also be introduced as an additional substitution into a single-chain insulin analogue as disclosed for example in U.S. Pat. No. 8,192,957.

Ortho-monofluoro-Phenylalanine (2F-Phe) was introduced within an engineered insulin monomer of native activity, designated DKP-insulin, which contains the substitutions $Asp^{B10}$ (D), $Lys^{B28}$ (K), and $Pro^{B29}$ (P). These three substitutions on the surface of the B chain are believed to impede formation of dimers and hexamers and to be incompatible with hexamer assembly in the absence or presence of zinc ions and in the absence or presence of a phenolic preservative. KP-insulin (which lacks the $Asp^{B10}$ substitution of DKP insulin) is the active ingredient of Humalog® (also designated insulin Lispro), currently in clinical use as a rapid-acting insulin analogue formulation. The sequence of the B-chain polypeptide for this variant of DKP-insulin is provided as SEQ ID NO: 6. Ortho-monofluoro-Phenylalanine (2F-Phe) was also introduced at position B24 within an engineered insulin monomer of enhanced activity, designated DDP-insulin, which contains the substitution $Asp^{B10}$ (D) in addition to the DP substitutions $Asp^{B28}$ (K) and $Pro^{B29}$ (P) in accordance with the general scheme provided in SEQ. ID. NO 4. $2F-Phe^{B24}$ was also introduced into non-standard human insulin analogues containing Ornithine position B29 in accordance with the general scheme provided in SEQ. ID. NO 5.

The above analogues of $Asp^{B10}$-insulin were prepared by trypsin-catalyzed semi-synthesis and purified by high-performance liquid chromatography (Mirmira, R. G., and Tager, H. S., 1989. *J. Biol. Chem.* 264: 6349-6354.) This protocol employs (i) a synthetic octapeptide representing residues (N)-GF*FYT<u>KP</u>T (including modified residue (F*) and "KP" substitutions (underlined); SEQ ID NO: 15) and (ii) truncated analogue des-octapeptide[B23-B30]-insulin or, in the case of DKP-insulin analogues, $Asp^{B10}$-des-octapeptide[B23-B30]-insulin (SEQ ID NO: 11). Because the octapeptide differs from the wild-type B23-B30 sequence (GF*FYTPKT; SEQ ID NO: 12) by interchange of $Pro^{B28}$ and $Lys^{B29}$ (italics), protection of the lysine ε-amino group is not required during trypsin treatment. In brief, des-octapeptide (15 mg) and octapeptide (15 mg) were dissolved in a mixture of dimethylacetamide/1,4-butandiol/0.2 M Tris acetate (pH 8) containing 10 mM calcium acetate and 1 mM ethylene diamine tetra-acetic acid (EDTA) (35:35:30, v/v, 0.4 mL). The final pH was adjusted to 7.0 with 10 μL of N-methylmorpholine. The solution was cooled to 12° C., and 1.5 mg of TPCK-trypsin was added and incubated for 2 days at 12° C. An additional 1.5 mg of trypsin was added after 24 hr. The reaction was acidified with 0.1% trifluoroacetic acid and purified by preparative reverse-phase HPLC (C4). Mass spectrometry using matrix-assisted laser desorption/ionization time-of-flight (MALDI-TOF; Applied Biosystems, Foster City, Calif.) in each case gave expected values (not shown). The general protocol for solid-phase synthesis is as described (Merrifield et al., 1982. *Biochemistry* 21: 5020-5031). 9-fluoren-9-yl-methoxy-carbonyl (F-moc)-protected phenylalanine analogues were purchased from Chem-Impex International (Wood Dale, Ill.).

The above protocol was also employed to prepare an analogue of $Asp^{B10}$-human insulin in which $Phe^{B24}$ was substituted by 2-F-Phe and in which $Pro^{B28}$ was substituted by Asp (D) and $Lys^{B29}$ was substituted by Pro (P). This analogue is designated $2F-Phe^{B24}$-DDP-insulin wherein the acronym DDP refers in turn to the identity of the amino-acid residue at respective positions B10, B28, and B29.

The above protocol was also employed to prepare an analogue of $Asp^{B10}$-human insulin containing Ornithine (O) at position B29 and to introduce $2F-Phe^{B24}$ in this context. The method of preparation of this analogue exploited the non-standard amino-acid substitution at position 29 to eliminate the tryptic site ordinarily present within the C-terminal octapeptide of the B chain (i.e., between $Lys^{B29}$ and $Thr^{B30}$) while maintaining a Proline (P) at position 28. $Pro^{B28}$ is believed to contribute to the stability of the dimer interface within the insulin hexamer, and so this method of preparation provides near-isosteric models of wild-type insulin in which other modifications may conveniently be incorporated without the need for cumbersome side-chain protection. This analogue is designated $2F-Phe^{B24}$-DPO-insulin wherein the acronym DPO refers, as above, to the identity of the amino-acid residue at respective positions B10, B28, and B29. The $2F-Phe^{B24}$-modified insulin analogues were subjected to some or all of the following assays. Biological potency was assessed in a diabetic rat model and by euglycemic clamp in anesthetized Yorkshire pigs; receptor-binding activity values shown are based on ratio of hormone-receptor dissociation constants relative to human insulin (the activity of human insulin is thus 1.0 by definition with standard errors in the activity values otherwise less in general than 25%); assays of hormone-stimulated autophosphorylation of the Type I IGF receptor were performed in a mouse embryo fibroblast expressing the human IGF-IR (kindly provided by Drs. Deepali Sachdev and Douglas Yee of the University of Minnesota); assays of mitogenicity in a human cell line employed breast-cancer-derived cell line MCF-7 as described (Milazzo G, Sciacca L, Papa V, Goldfine I D, Vigneri R. (1997) $Asp^{B10}$-insulin induction of increased mitogenic responses and phenotypic changes in human breast epithelial cells: evidence for enhanced interactions with the insulin-like growth factor-I receptor. *Mol. Carcinog.* 18, 19-25); thermodynamic stability values (free energies of unfolding; $\Delta G_u$) were assessed at 25° C. based on a two-state model as extrapolated to zero denaturant concentration; resistance to fibril formation was evaluated by measurement of lag times (in days) required for initiation of protein fibrillation on gentle agitation at 30° C. in zinc-free phosphate-buffered saline (pH 7.4) as described (Yang, Y., Petkova, A. T., Huang, K., Xu, B., Hua, Q. X., Y, I. J., Chu, Y. C., Hu, S. Q., Phillips, N. B., Whittaker, J., Ismail-Beigi, F., Mackin, R. B., Katsoyannis, P. G., Tycko, R., & Weiss, M. A. (2010) An Achilles' Heel in an amyloidogenic protein and its repair. Insulin fibrillation and therapeutic design. *J. Biol. Chem.* 285, 10806-10821). Results of curve fitting are summarized in Table 4 and illustrated in FIG. 8.

Figure 7:
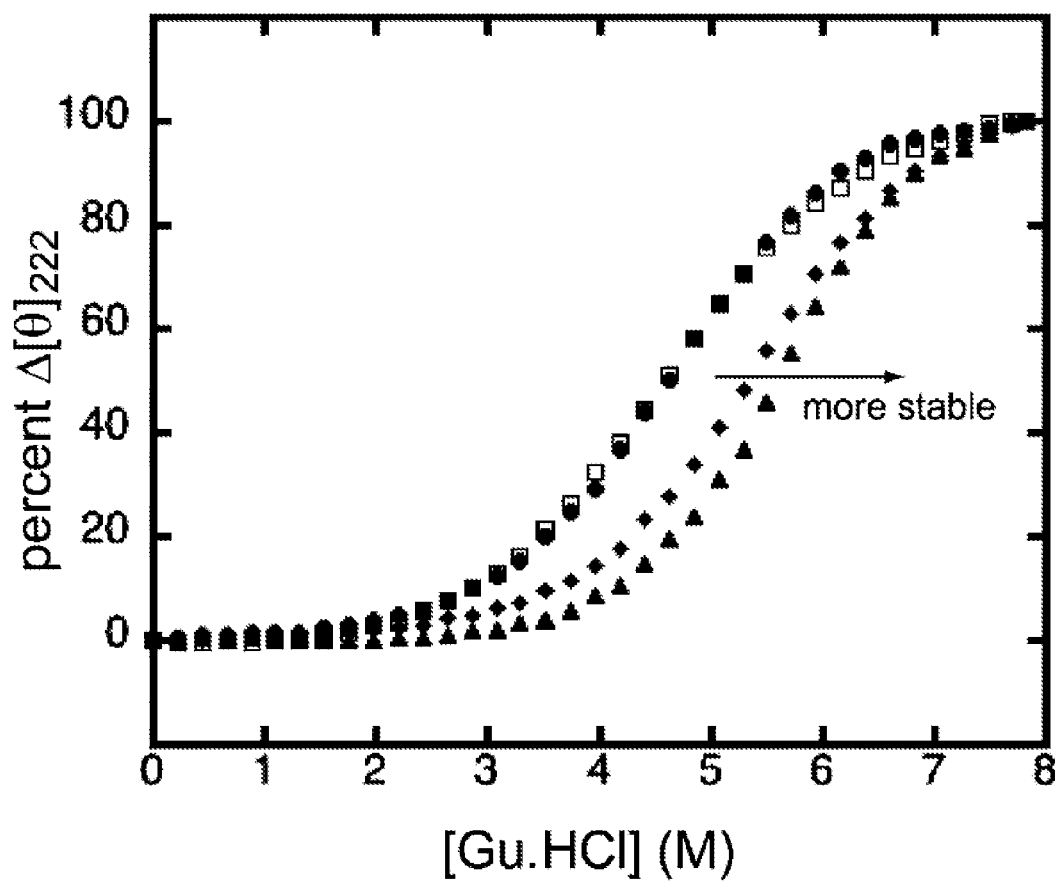
FIG. 7 provides a graph of CD-detected guanidine denaturation. Chemical denaturation of human insulin (HI, ●), insulin Lispro (KP, □), $Asp^{B10}$-KP-insulin (DKP, ♦) and 2F-$Phe^{B24}$-DKP-insulin (▲) insulin analogs. Spectra were collected at 25° C. in phosphate-buffer saline (pH 7.4). Unfolding was monitored by CD at 222 nm. The stability of the 2F-$Phe^{B24}$-DKP analogue exhibits a gain of 0.6(±0.2) and 1.6(±0.2) kcal/mol in stability ($\Delta\Delta G_u$) relative to DKP-insulin and human insulin, respectively (see Table 4).

Circular dichroism (CD) spectra were obtained at 4° C. and/or 25° C. using an Aviv spectropolarimeter (Weiss et al., *Biochemistry* 39: 15429-15440). Samples contained ca. 25 µM DKP-insulin or analogues in 50 mM potassium phosphate (pH 7.4); samples were diluted to 5 µM for guanidine-induced denaturation studies at 25° C. To extract free energies of unfolding, denaturation transitions were fitted by non-linear least squares to a two-state model as described by Sosnick et al., *Methods Enzymol.* 317: 393-409. In brief, CD data θ(x), where x indicates the concentration of denaturant, were fitted by a nonlinear least-squares program according to $$\theta(x) = \frac{\theta_A + \theta_B e^{(-\Delta G^o_{H_2O} - mx)/RT}}{1 + e^{-(\Delta G^o_{H_2O} - mx)/RT}}$$

where x is the concentration of guanidine and where $\theta_A$ and $\theta_B$ are baseline values in the native and unfolded states. Baselines were approximated by pre- and post-transition lines $\theta_A(x)=\theta_A^{H_2O}+m_A x$ and $\theta_B(x)=\theta_B^{H_2O}+m_B x$. The m values obtained in fitting the variant unfolding transitions are lower than the m value obtained in fitting the wild-type unfolding curve. To test whether this difference and apparent change in $\Delta G_u$ result from an inability to measure the CD signal from the fully unfolded state, simulations were performed in which the data were extrapolated to plateau CD values at higher concentrations of guanidine; essentially identical estimates of $\Delta G_u$ and m were obtained. Representative data are shown in FIG. 7. The far-ultraviolet circular dichroism (CD) spectrum of the 2F-Phe$^{B24}$-DKP-insulin analogue is similar to those of the parent analogue DKP-insulin.

Figure 8:
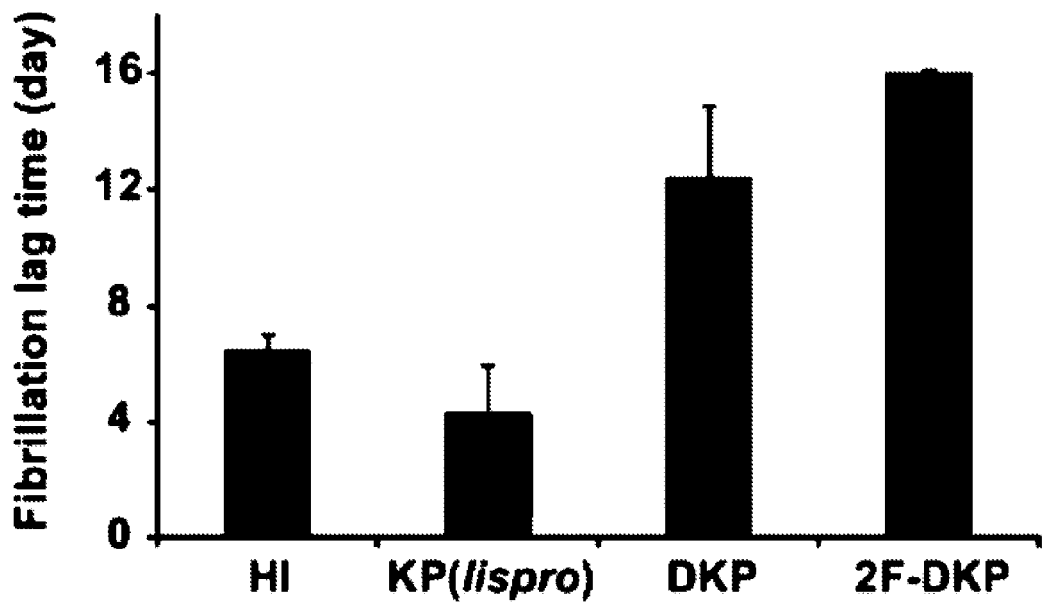
FIG. 8 is a histogram comparing the fibrillation lag times of insulin analogues. Thioflavin T fluorescence monitored fibrillation lag time. Samples were gently agitated at 37° C. and pH 7.4 in Zn-free phosphate-buffered saline. 2F-DKP-insulin was 3.7 and 2.4-fold more resistant to fibrillation (as probed by lag times) relative to insulin Lispro and wild-type human insulin, respectively.

The baseline thermodynamic stability of KP-insulin, as inferred from a two-state model of denaturation at 25° C., is 3.0±0.1 kcal/mole. CD-detected guanidine denaturation studies indicate that the 2F-Phe$^{B24}$ substitution is associated with a gain in thermodynamic stability in the context of KP-insulin ($\Delta\Delta G_u$ 1.1±0.2 kcal/mole) and in the context of DKP-insulin ($\Delta\Delta G_u$ 0.60±0.2 kcal/mole). Further, the physical stability of the 2F-Phe$^{B24}$-DKP-insulin was found to be markedly greater than that of KP-insulin as evaluated in triplicate during incubation; the proteins were made 300 µM in phosphate-buffered saline (PBS) at pH 7.4 at 30° C. under gentle agitation. The samples were observed for 20 days or until signs of precipitation or frosting of the glass vial were observed. Results are shown in FIG. 8 (see also Table 4).

Figure 4:
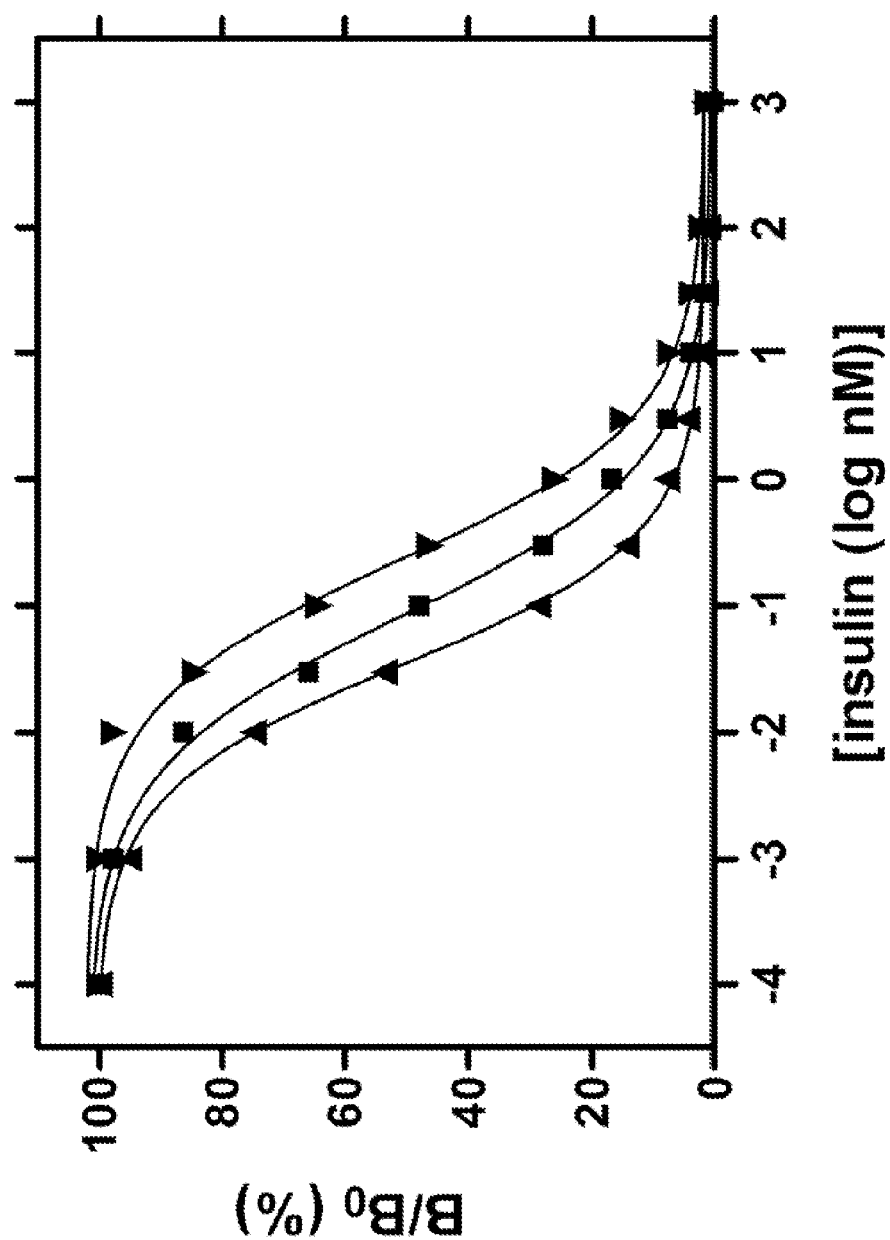
FIG. 4 is a graph showing the results of receptor-binding studies of insulin analogues. Relative activities for the B isoform of the insulin receptor (IR-B) are determined by competitive binding assay in which receptor-bound $^{125}$I-labeled human insulin is displaced by increasing concentrations of human insulin (●) or its analogues: DKP-insulin (▲) and 2F-$Phe^{B24}$-DKP-insulin (▼); results of curve fitting are summarized in Tables 2 and 3.

Relative receptor-binding activity is defined as the ratio of the hormone-receptor dissociation constants of analogue to wild-type human insulin, as measured by a competitive displacement assay using $^{125}$I-human insulin. Microtiter strip plates (Nunc Maxisorb) were incubated overnight at 4° C. with AU5 IgG (100 µl/well of 40 mg/ml in phosphate-buffered saline). Binding data were analyzed by a two-site sequential model. Data were corrected for nonspecific binding (amount of radioactivity remaining membrane associated in the presence of 1 µM human insulin. In all assays the percentage of tracer bound in the absence of competing ligand was less than 15% to avoid ligand-depletion artifacts. Representative data are provided in FIG. 4.

To assess hypoglycemic potencies of DKP-insulin analogues, DDP-insulin analogues, and DPO insulin analogues or there 2F-Phe$^{B24}$ derivatives relative to KP-insulin or wild-type human insulin in vivo, male Lewis rats (mean body mass ~300 grams) were rendered diabetic by treatment with streptozotocin. (This model provides a probe of potency but not degree of acceleration of pharmacokinetics as (i) wild-type insulin, KP-insulin, and Asp$^{B28}$-insulin exhibit similar patterns of effects of blood glucose concentration and (ii) these patterns are unaffected by the presence of absence of zinc ions in the formulation at a stoichiometry sufficient to ensure assembly of insulin hexamers.) Protein solutions containing wild-type human insulin, insulin analogues, or buffer alone (protein-free sterile diluent obtained from Eli Lilly and Co.; composed of 16 mg glycerin, 1.6 mg meta-cresol, 0.65 mg phenol, and 3.8 mg sodium phosphate at pH 7.4) were injected subcutaneously, and resulting changes in blood glucose were monitored by serial measurements using a clinical glucometer (Hypoguard Advance Micro-Draw meter). To ensure uniformity of formulation, insulin analogues were each re-purified by reverse-phase high-performance liquid chromatography (rp-HPLC), dried to powder, dissolved in diluent at the same maximum protein concentration (300 µg/mL) and re-quantitative by analytical C4 rp-HPLC; dilutions were made using the above buffer. Rats were injected subcutaneously at time t=0 with 20 µg insulin in 100 µl of buffer per 300 g rat. This dose corresponds to ca. 67 µg/kg body weight, which corresponds in international units (IU) to 2 IU/kg body weight. Dose-response studies of KP-insulin indicated that at this dose a near-maximal rate of glucose disposal during the first hour following injection was achieved. Five rats were studied in the group receiving 2F-Phe$^{B24}$-DKP-insulin, 2F-Phe$^{B24}$-DDP-insulin, or 2F-Phe$^{B24}$-DPO, and five different rats were studied in the control group receiving KP-insulin or wild-type human insulin; these rats were randomly selected from a colony of 30 diabetic rats. The two groups exhibited similar mean blood glucose concentrations at the start of the experiment. Blood was obtained from clipped tip of the tail at time 0 and every 10 minutes up to 90 min; in some studies the time period was extended to 180 min or 240 min. The efficacy of insulin action to reduce blood glucose concentration was calculated using the change in concentration over time (using least-mean squares and initial region of linear fall) divided by the concentration of insulin injected. These data thus suggest that the biological potency of 2F-Phe$^{B24}$-DKP-insulin is equivalent to that of KP-insulin in a zinc hexamer formulation; the other 2F-Phe$^{B24}$ insulin analogues were not tested in the rat model.

To assess PK, PD, and potency of insulin analogues in an animal model predictive of pharmacologic properties in humans, 2F-Phe$^{B24}$ derivatives of Asp$^{B10}$-containing human insulin analogues were investigated in adolescent Yorkshire farm pigs (weight 35-45 kg). On the day of study, each animal underwent anesthesia induction with Telazol and general anesthesia with isoflurane. Each animal was endotreacheally intubated with continuous monitoring of oxygen saturation and end-tidal expired $CO_2$. Although the animals were not diabetic, islet function was suppressed in the OR by subcutaneous injection of octreotide acetate (44 mg/kg) approximately 30 min before beginning the clamp study and every 2 h thereafter. After IV catheters were placed and baseline euglycemia established with 10% dextrose infusion, an subcutaneous injection of the insulin was given through the catheter. In order to quantify peripheral insulin-mediated glucose uptake, a variable-rate glucose infusion was given to maintain a blood glucose concentration of approximately 85 mg/dl. This glucose infusion typically will be required for 5-6 hours, i.e., until in control studies of Humulin® glucose infusion rates were typically observed to return to pre-insulin baseline values. Glucose concentrations were measured with a Hemocue 201 portable glucose analyzer every 10 min (with standard error 1.9%).

Figure 9:
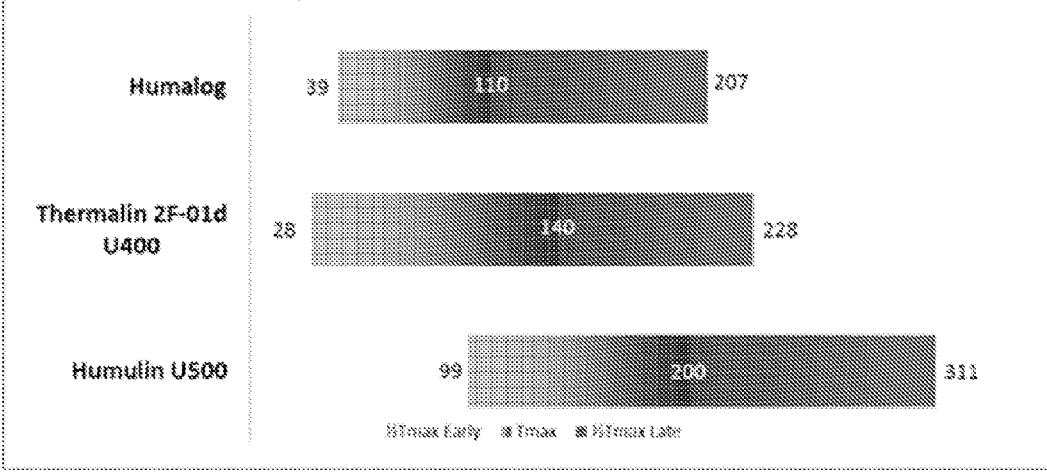
FIG. 9 provides a graphical summary of the pharmacodynamics in anesthetized pigs of 2F-$Phe^{B24}$-DKP-insulin at U-400 strength (in zinc-free Lilly diluent containing 5 mM ethylenediaminetetraacetic acid (EDTA) at pH 7.4; middle bar) in relation to current insulin products Humalog (U-100 strength; top bar) and Humulin R U-500 (bottom bar).

The computerized protocol for glucose clamping was as described (Matthews, D. R., and Hosker, J. P. (1989) *Diabetes Care* 12, 156-159). In brief, 2-ml blood samples for insulin assay were obtained according to the following schedule: from 0-40 min after insulin delivery: 5-minute intervals; from 50-140 min: 10-minute intervals, and from 160 min—to the point when GIR is back to baseline: 20-min intervals. For PK/PD a 20-min moving mean curve fit and filter is applied. PD was measured as time to half-maximal effect (early), time to half-maximal effect (late), time to maximal effect, and area-under-the-curve (AUC) over baseline. For each of these analyses, the fitted curve, not the raw data, were employed in subsequent analyses. Each of three pigs underwent two studies: one with Chlorolog and one at the same dosage (0.5 max dose) with U-500 comparator Humulin® R U-500 (Eli Lilly and Co., Indianapolis, Ind.) and U-100 comparators Humalog® and control Humulin® (Lilly Laboratories, Indianapolis, Ind.). The results indicate that 2F-PheB$^{24}$-DKP-insulin and 2F-PheB$^{24}$-DDP-insulin retain rapid-acting PD when concentrated to U-400 strength (2.4 mM; 2F-PheB$^{24}$-DKP-insulin) or U-500 strength (3.0 mM; 2F-PheB$^{24}$-DDP-insulin). PD parameters are summarized in Table 1 and in graphical form in FIG. 9.

TABLE 1

PD Studies of 2F-Phe$^{B24}$ Analogues in Anesthetized Yorkshire Pigs[a]

| Protein | Strength | Additive | (1/2)T$_{max}$ (early) | T$_{max}$ | (1/2)T$_{max}$ (late) |
|---|---|---|---|---|---|
| A. Control Studies of Humulin ® R U-500 (pigs 1-4)[b] | | | | | |
| wild-type | U-500 | none | 122 min | 240 min | 357 min |
| wild-type | U-500 | none | 77 min | 180 min | 342 min |
| wild-type | U-500 | none | 100 min | 180 min | 342 min |
| wild-type | U-500 | none | 95 min | 200 min | 217 min |
| B. Studies of 2F-Phe$^{B24}$-DKP-insulin (pig 5)[c] | | | | | |
| KP-insulin | U-100 | none[d] | 61 min | 120 min | 193 min |
| 2F-DKP-ins | U-100 | none | 62 min | 130 min | 186 min |
| KP-insulin | U-400 | EDTA[e] | 105 min | 190 min | 274 min |
| 2F-DKP-ins | U-400 | EDTA[f] | 28 min | 140 min | 228 min |
| C. Studies of 2F-Phe$^{B24}$-DDP-insulin (pig 6)[g] | | | | | |
| KP-insulin | U-100 | none[d] | 36 min | 100 min | 160 min |
| 2F-DDP-ins | U-100 | EDTA[h] | 33 min | 100 min | 172 min |
| D. Studies of 2F-Phe$^{B24}$-DDP-insulin (pig 7)[g] | | | | | |
| wild-type | U-500[b] | none | 95 min | 200 min | 271 min |
| 2F-DDP-ins | U-500 | EGTA[i] | 76 min | 180 min | 280 min | aPD, pharmacodynamics.
Key results are shown in bold.
[b]Four different pigs were used in control studies of Lilly U-500 as formulated by the manufacturer (part A). These animals differed in turn from used in the studies of 2F-Phe$^{B24}$ analogs; the various pigs were nonetheless similar in age and body mass.
[c]The three trials of 2F-Phe$^{B24}$-DKP-insulin (abbreviated 2F-DKP-ins) were conducted in a single pig.
[d]KP-insulin was as formulated by the manufacturer (Humalog ®; Eli Lilly and Co.).
[e]EDTA was added to a concentration of 5 mM to the formulation buffer used in the Lilly U-100 Humalog ® product.
[g]This analogue is abbreviated as 2F-DDP-ins.
[h]EDTA was added to a concentration of 5 mM to a zinc-free formulation in which phosphate buffer was replaced by THAM buffer (2-amino-2-hydroxymethyl-propane-1, 3-diol); the formulation was otherwise similar to Lilly Diluent.

Figure 5:
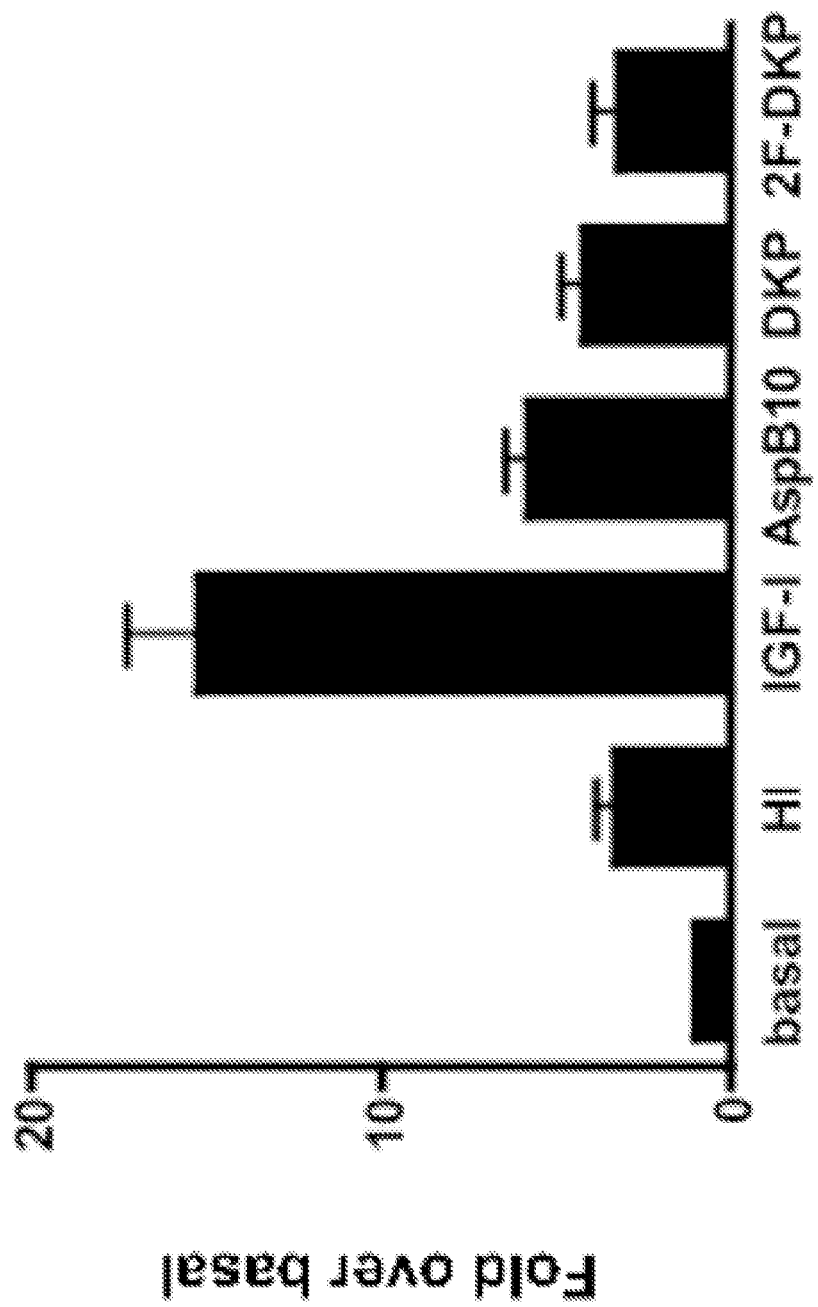
FIG. 5 is a histogram showing extent of ligand-stimulated IGF-I receptor autophosphorylation. IGF-I receptor-deficient mouse embryo fibroblast cells stably expressing the human IGF-I receptor were serum-starved overnight and then treated with 10 nM ligand for 5 min and cell lysates prepared and analyzed for phosphorylated IGF-I receptor (IGF-IR) by ELISA. Autophosphorelation by 2F-DKP is similar with HI.
Figure 6:
FIG. 6 shows the results of a breast-cancer-related MCF-7 colony formation assay for mitogenecity. MCF-7 human breast cancer cells were analyzed for colony formation in soft agar (reflecting tumorigenic potential) in the presence of 10 nM ligands after 1-week growth. Tumergenic potential of 2F-$Phe^{B24}$-DKP was comparable to wild-type human insulin and untreated cells.

Because the Asp$^{B10}$ substitution in the context of unmodified human insulin (Asp$^{B10}$-insulin) was observed to exhibit enhanced mitogenicity relative to wild-type insulin in associated with excess mammary tumor formation in Sprague-Dawley rats (Oleksiewicz, M. B., Bonnesen, C., Hegelund, A. C., Lundby, A., Holm, G. M., Jensen, M. B., & Krabbe, J. S. (2011) Comparison of intracellular signalling by insulin and the hypermitogenic Asp$^{B10}$ analogue in MCF-7 breast adenocarcinoma cells. *J. Appl. Toxicol.* 31, 329-41 and references therein), we undertook mammalian cell-based studies of hormone-stimulated autophosphorylation of the Type I IGF receptor (IGF-IR) in a mouse embryo fibroblast cell lacking endogenous IGF receptors and stably transfected to express human IGF-IR; results are illustrated in FIG. 5. The cells were grown to 75% confluence, starved of serum overnight and then treated with 10 nM hormone (wild-type insulin, IGF-I, Asp$^{B10}$-insulin, Asp$^{B10}$-Orn$^{B29}$-insulin, DKP-insulin, 2F-Phe$^{B24}$-DKP-insulin, or 2F-Phe$^{B24}$-DPO-insulin). Cell lysates were in each case prepared and analyzed for phosphorylated IGF-I receptor by anti-phospho-IGF-IR ELISA as described by the vendor (Cell Signaling Technologies, Inc.). Studies were performed in triplicate. The results demonstrate that whereas Asp$^{B10}$-insulin exhibits more profound autophosphorylation relative to human insulin, the 2F-Phe$^{B24}$ modification restores the level of autophosphorylation to that indistinguishable from that of wild-type human insulin. Further, the set of hormones and analogues was tested for their ability to stimulate the proliferation of human breast-cancer cell line MCF-7 as described (Milazzo G, Sciacca L, Papa V, Goldfine I D, Vigneri R. (1997) Asp$^{B10}$-insulin induction of increased mitogenic responses and phenotypic changes in human breast epithelial cells: evidence for enhanced interactions with the insulin-like growth factor-I receptor. *Mol. Carcinog.* 18, 19-25). The cancer cells were analyzed for colony formation in soft agar (reflecting tumorigenic potential) in the presence of 10 nM ligands after 1 week of growth; results are illustrated in FIG. 6. Whereas Asp$^{B10}$-insulin stimulates more growth than does wild-type human insulin, the further addition of the 2F-Phe$^{B24}$ modification reduces mitogenicity to a level indistinguishable from that of wild-type human insulin.

Structural accommodation of the 2F-Phe$^{B24}$ modification was analyzed in a monomeric context through 2D-NMR studies of 2F-Phe$^{B24}$-DKP-insulin. A native-like pattern of $^1$H-NMR chemical shifts and nuclear Overhauser effects (NOEs) was observed; molecular models based on distance-geometry and simulated annealing were similar to those obtained in 2D-NMR studies of DKP-insulin. Additional structural studies were undertaken by single-crystal X-ray crystallography. Crystals based on zinc KP-insulin hexamers were grown as described (Liu, M., Wan, Z., Chu, Y. C., Aladdin, H., Klaproth, B., Choguette, M., Hua, Q. X., Mackin, R., Rao, J. S., De Meyts, P., Katsoyannis, P. G., Aryan, P. & Weiss, M. A. (2009) The crystal structure of a "nonfoldable" insulin: impaired folding efficiency despite native activity. *J. Biol. Chem.* 284, 35259-35272). In brief, crystals were grown by hanging-drop vapor diffusion in the presence of a 1:2.5 ratio of Zn$^{2+}$ to protein monomer and a 3.7:1 ratio of phenol to protein monomer in Tris-HCl buffer. Drops consisted of 1 µl of protein solution (10 mg/ml in 0.02 M HCl) mixed with 1 µl of reservoir solution (0.02 M Tris-HCl, 0.05 M sodium citrate, 5% acetone, 0.03% phenol, and 0.01% zinc acetate at pH 8.1). Each drop was suspended over 1 ml of reservoir solution. Crystals (space group R3) were obtained at room temperature after two weeks. Data were collected from single crystals mounted in a rayon loop and flash frozen to 100 K. Reflections from 24.98-2.50 Å were measured on CCD detector system on synchrotron radiation at Advanced Photon Source (APS) at Argonne National Laboratory, Chicago. Data were processed with programs HKL2000 (Z. Otwinowski and W. Minor (1997) Processing of X-ray Diffraction Data Collected in Oscillation Mode", *Methods in Enzymology*, Volume 276: Macromolecular Crystallography [C. W. Carter, Jr. & R. M. Sweet, Eds.], Academic Press (New York), part A, pp. 307-26). The crystal exhibited unit-cell parameters: a=b=77.98 Å, c=37.14 Å, α=β=90°, γ=120°. The structure was determined by molecular replacement using CNS. Accordingly, a model was obtained using the native TR dimer (Protein Databank (PDB) identifier 1LPH following removal of all water molecules, zinc and chloride ions). A translation-function search was performed using coordinates from the best solution for the rotation function following analysis of data between 15.0 and 4.0 Å resolutions. Rigid-body refinement using CNS, employing overall anisotropic temperature factors and bulk-solvent correction, yielded values of 0.29 and 0.33 for R and $R_{free}$, respectively, for data between 25.0 and 3.0 Å resolution. Between refinement cycles, $2F_o$–$F_c$ and $F_o$–$F_c$ maps were calculated using data to 2.50 Å resolution; zinc and chloride ions and phenol molecules were built into the structure using the program O. The geometry was continually monitored with PROCHECK; zinc ions and water molecules were built into the difference map as the refinement proceeded. Calculation of omit maps (especially in the first eight residues of B chain N terminus of each monomer) and further refinement were carried out using CNS, which implement maximum-likelihood torsion-angle dynamics and conjugate-gradient refinement.

Figure 10:
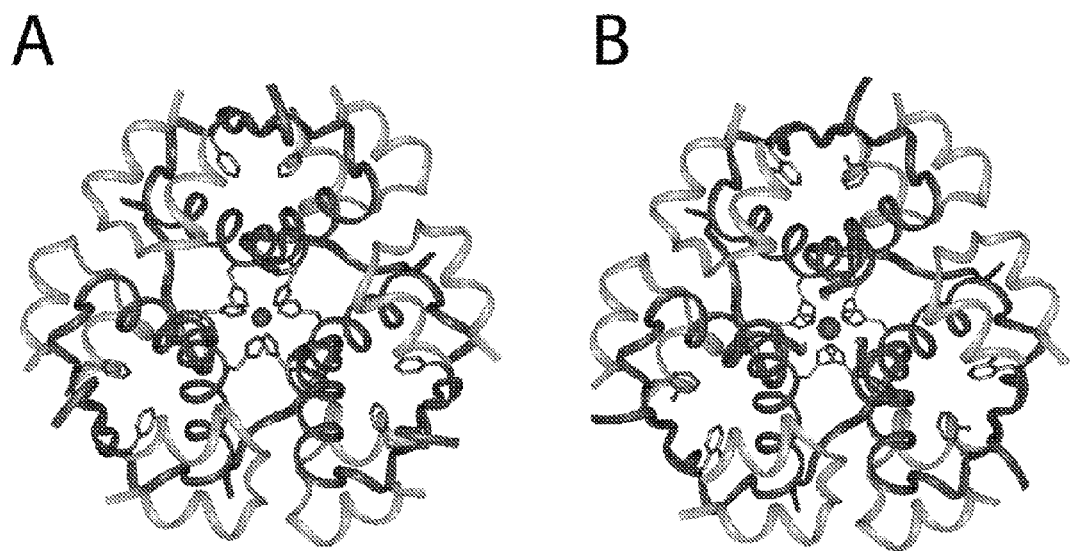
FIG. 10 provides a structural depiction of the crystal structure of 2F-Phe$^{B24}$ in the context of a zinc KP-insulin hexamer. (A) Ribbon model of wild-type human insulin as a $T_3R^f_3$ zinc hexamer. (B) Corresponding ribbon model of 2F-Phe$^{B24}$-KP-insulin in the same crystal form. The variant $T_3R^f_3$ structure is similar to that of the parent hexamer, demonstrating lack of long-range structural perturbations and accommodation of the fluorine atom at a native-like dimer interface.
Figure 11:
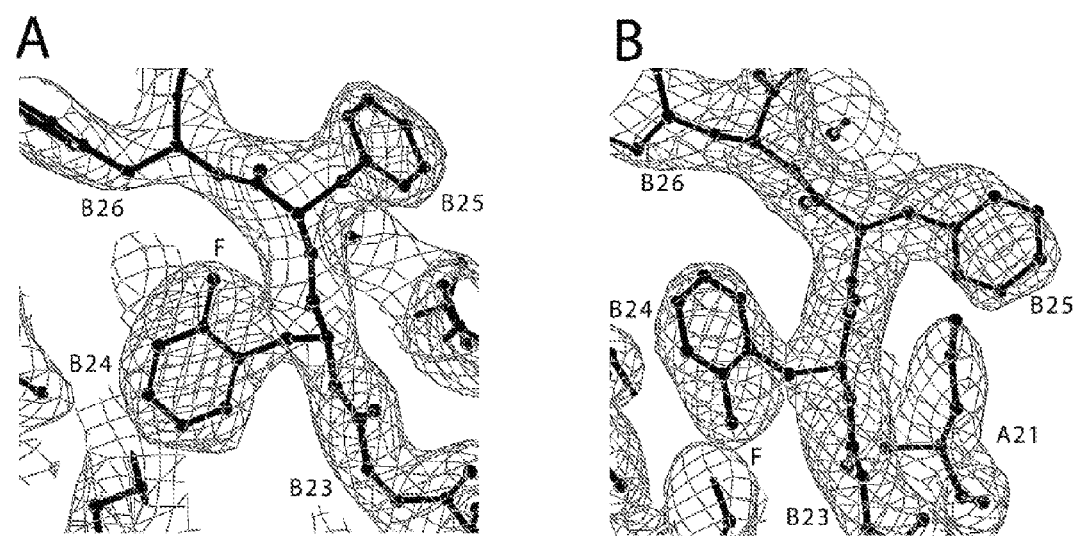
FIG. 11 illustrates the electron density surrounding 2F-Phe$^{B24}$ in the crystal structure of 2F-Phe$^{B24}$ as determined at a resolution of 2.5 Å. (A) 2F-Phe$^{B24}$ and neighboring electron density in the T-state protomer. (B) 2F-Phe$^{B24}$ and neighboring electron density in the $R^f$-state protomer. The orientation of the B24 ring and interactions of the fluoro moiety differ between the two conformational states.

The structures are similar to those of the parent analog as illustrated in FIG. 10. Whereas the location of the aromatic ring is similar to that of the unmodified residue in wild-type insulin, the T and Rf-state protomers exhibit distinct conformations as illustrated by the electron-density maps shown in FIG. 11. In each case the orientation of the 2F-Phe$^{B24}$ aromatic ring with respect to an individual insulin protomer leaves a native-like outer dimerization interface. Irrespective of theory, a T-like orientation was also observed in 2D-NMR studies of the monomeric 2F-Phe$^{B24}$-DKP-insulin analogue and is likely to accrue favorable electrostatic interactions, thereby rationalizing the increased thermodynamic stabilities of 2F-Phe$^{B24}$ insulin analogues. In this conformation the electronegative fluoro-substituent is near the partial positive charges of two amide nitrogens (the main-chain peptide NH moieties of Phe$^{B25}$ and Tyr$^{B26}$).

To test the compatibility of the 2F-Phe$^{B24}$ modification with dimerization (as pertinent to 2F-PheB$^{24}$-DPO-insulin and related analogues in which residues B28 and B29 do not impair dimerization), the 2F-Phe$^{B24}$ modification was introduced into framework otherwise capable of hexamer formation to enable spectroscopic analysis of cobalt-mediated (Co$^{2+}$) hexamer assembly and the kinetic analysis of hexamer disassembly. The kinetic stability of insulin analogue hexamers was assessed at 25° C. relative to that of the wild-type human insulin hexamer as a Co$^{2+}$ complex in the presence of 2.2 cobalt ions per hexamer and 50 mM phenol in a buffer consisting of 10 Tris-HCl (pH 7.4). The assay, a modification of the procedure of Beals et al. (Birnbaum, D. T., Kilcomons, M. A., DeFelippis, M. R., & Beals, J. M. Assembly and dissociation of human insulin and Lys$^{B28}$ Pro$^{B29}$-insulin hexamers: a comparison study. *Pharm Res.* 14, 25-36 (1997)), employs optical absorbance at 500-700 nm to monitor the $R_6$-hexamer-specific d-d transitions characteristic of tetrahedral cobalt ion coordination. Although the solution at equilibrium contains a predominance of cobalt insulin hexamers or cobalt insulin analogue hexamers, this equilibrium is characterized by opposing rates of insulin assembly and disassembly. To initiate the assay, the solution is made 2 mM in ethylene-diamine-tetra-acetic acid (EDTA) to sequester free cobalt ions. The time course of decay of the $R_6$-specific absorption band on addition of EDTA provides an estimate of the rate of hexamer disassembly. Whereas wild-type insulin exhibited a time constant of 419±51 seconds, KP-insulin exhibited a time constant of 114±13 seconds in accordance with its accelerated pharmacokinatics. Strikingly, the baseline absorption spectrum of 2F-Phe$^{B24}$-DPO-insulin is similar to that of wild-type human insulin, indicating that the 2F-Phe$^{B24}$ modification does not prevent formation of a native-like dimer interface.

Structural accommodation of the 2F-Phe$^{B24}$ modification was analyzed in a monomeric context through 2D-NMR studies of 2F-Phe$^{B24}$-DKP-insulin. A native-like pattern of $^1$H-NMR chemical shifts and nuclear Overhauser effects (NOEs) was observed; molecular models based on distance-geometry and simulated annealing were similar to those obtained in 2D-NMR studies of DKP-insulin. Additional structural studies were undertaken by single-crystal X-ray crystallography. Crystals based on zinc KP-insulin hexamers were grown as described (Liu, M., Wan, Z., Chu, Y. C., Aladdin, H., Klaproth, B., Choguette, M., Hua, Q. X., Mackin, R., Rao, J. S., De Meyts, P., Katsoyannis, P. G., Aryan, P. & Weiss, M. A. (2009) The crystal structure of a "nonfoldable" insulin: impaired folding efficiency despite native activity. *J. Biol. Chem.* 284, 35259-35272). The structures are similar to those of the parent analogue as illustrated in FIG. 10. In particular, the inward orientation of the 2F-Phe$^{B24}$ aromatic ring with respect to an individual insulin protomer leaves a native-like outer dimerization interface. Irrespective of theory, this inward orientation was also observed in 2D-NMR studies of the monomeric 2F-Phe$^{B24}$-DKP-insulin analogue and is likely to accrue favorable electrostatic interactions, thereby rationalizing the increased thermodynamic stabilities of 2F-Phe$^{B24}$ insulin analogues.

Dissociation constants ($K_d$) were determined as described by Whittaker and Whittaker (2005. *J. Biol. Chem.* 280: 20932-20936), by a competitive displacement assay using $^{125}$I-Tyr$^{414}$-insulin (kindly provided by Novo-Nordisk) and the purified and solubilized insulin receptor (isoform B or A) in a microtiter plate antibody capture assay with minor modification; transfected receptors were tagged at their C-terminus by a triple repeat of the FLAG epitope (DYKDDDDK) and microtiter plates were coated by anti-FLAG M2 monoclonal antibody (Sigma). The percentage of tracer bound in the absence of competing ligand was less than 15% to avoid ligand-depletion artifacts. Binding data (illustrated in FIG. 5) were analyzed by non-linear regression using a heterologous competition model (Wang, 1995, *FEBS Lett.* 360: 111-114) to obtain dissociation constants. Results are provided in Table 2 (2F-Phe$^{B24}$ KP-insulin analogue relative to KP-insulin) and Table 3 (templates DKP, DDP, and DPO; see footnote to Table 3); dissociation constants are provided in units of nanomolar. (The two studies were conducted on different dates with different preparations of insulin receptor (IR isoform B; IR-B) and IGF receptor (IGF-IR) and so are tabulated independently.) The 2F-Phe$^{B24}$ modification of KP-insulin reduces IR-B receptor-binding affinities by between twofold and threefold; such small reductions are typically associated with native or near-native hypoglycemic potencies in vivo as demonstrated herein in diabetic Lewis rats. No significant increase was observed in the cross-binding of 2F-Phe$^{B24}$-KP-insulin to IGF-IR. The 2F-Phe$^{B24}$ modification of DKP-insulin reduces IR-B receptor-binding affinities by less than twofold; a trend toward increased cross-binding to IGF-IR was observed near the limit of statistical significance.

TABLE 2

Binding of Insulin Analogues to Insulin Receptor and IGF Receptor

| Protein | IR-B binding | IGF-1R binding |
|---|---|---|
| insulin | 0.063 ± 0.014 nM | 5.6 ± 0.9 nM |
| KP-insulin | 0.062 ± 0.011 nM | 8.2 ± 1.2 nM |
| 2F-Phe$^{B24}$-KP-insulin | 0.472 ± 0.011 nM | 34.1 ± 1.2 nM |

IR-B, B isoform of the insulin receptor;
IGF-1R, Type 1 IGF receptor

TABLE 3

Binding of Insulin Analogues to Insulin Receptor and IGF Receptor

| Protein | IR-B binding | IGF-1R binding |
|---|---|---|
| A. DKP Template | | |
| Insulin* | 0.063 ± 0.014 nM | 5.6 ± 0.9 nM |
| DKP-insulin | 0.020 ± 0.003 nM | 1.8 ± 0.3 nM |
| 2F-Phe$^{B24}$-DKP-insulin | 0.131 ± 0.020 nM | 9.2 ± 1.2 nM |
| B. DDP Template | | |
| insulin | 0.059 ± 0.010 nM | 3.7 ± 0.6 nM |
| KP-insulin | 0.064 ± 0.009 nM | 6.2 ± 1.2 nM |
| 2F-Phe$^{B24}$-DDP-insulin | 0.063 ± 0.010 nM | 4.8 ± 0.8 nM |
| C. DPO Template | | |
| insulin | 0.048 ± 0.008 nM | 3.1 ± 0.5 nM |
| Asp$^{B10}$-Orn$^{B29}$-insulin | 0.020 ± 0.014 nM | 1.2 ± 0.2 nM |
| 2F-Phe$^{B24}$-DPO-insulin | 0.082 ± 0.012 nM | 4.0 ± 0.6 nM |

IR-B, B isoform of the insulin receptor.
*Value obtained from Table 2.

The binding affinities of analogues containing the non-standard amino acid Ornithine at position B29 were similarly tested, both with and without a 2F-Phe substitution at B24. Results are provided in Table 3 as dissociation constants relative to the human insulin receptor isoform B (hIR-B), and human IGF receptor (hIGFR). While Orn$^{B29}$ has similar binding affinities for each receptor as wild type insulin, Nle$^{B29}$ has a decreased affinity for hIR-B and IGFR relative to wild type insulin. An analogue containing Orn$^{B29}$ in combination with 2F-Phe$^{B24}$, however, had decreased binding affinity for both isoforms of insulin receptor and slightly increased affinity for hIGFR. The 2F-Phe$^{B24}$, Nle$^{B29}$ analogue had similar binding affinity for hIGFR as the Nle$^{B29}$ only analogue, but had decreased binding affinity for hIR-B.

TABLE 4

Thermodynamic Stabilities of Insulin Analogues

| protein | $\Delta G_u$ (kcal/mole) | protein | $\Delta G_u$ (kcal/mole) |
|---|---|---|---|
| insulin | 3.6 ± 0.1 | 2F-insulin$^b$ | ND |
| KP-insulin | 2.8 ± 0.1 | 2F-KP-insulin | 3.6 ± 0.1 |
| DKP-insulin | 4.3 ± 0.1 | 2F-DKP-insulin | 4.9 ± 0.1 |
| DDP-insulin | ND$^a$ | 2F-DDP-insulin | 4.7 ± 0.1 |
| Orn$^{B29}$-insulin | ND$^a$ | 2F-Orn$^{B29}$-insulin | 4.0 ± 0.1 |
| DPO-insulin | ND$^a$ | 2F-DPO-insulin | 5.0 ± 0.1 |

$^a$Free energies of unfolding ($\Delta G_u$) were inferred from CD-detected guanidine denaturation studies based on application of a two-state model. ND, not determined.
$^b$2F designates the modification 2F-phe$^{B24}$ in insulin (also designated ortho-monofluoro-Phe$^{B24}$).
Analogue abbreviations:
DDP, substitutions [Asp$^{B10}$, Asp$^{B28}$, Pro$^{B29}$];
DKP, substitutions [Asp$^{B10}$, Lys$^{B28}$, Pro$^{B29}$];
DPO, substitutions [Asp$^{B10}$, Orn$^{B29}$] with Pro at position B28 as in wild-type insulin;
KP, substitutions [Lys$^{B28}$, Pro$^{B29}$]; and
Orn, ornithine.

A method for treating a patient comprises administering an insulin analogue containing a 2F-Phe$^{B24}$ modification or additional amino-acid substitutions in the A or B chain as known in the art or described herein. In one example, the 2F-Phe$^{B24}$ substituted insulin analogue is an insulin analogue containing 2F-Phe at position B24 in the context of DKP-insulin. In another example, 2F-Phe$^{B24}$ is substituted within Asp$^{B10}$-human insulin analogues containing non-standard modifications at position B29 (Ornithine or Norleucine). It is yet another aspect of the present invention that use of non-standard amino-acid substitutions enables a rapid and efficient method of preparation of insulin analogues by trypsin-mediated semi-synthesis using unprotected octapeptides.

In still another example, the insulin analogue is administered by an external or implantable insulin pump. An insulin analogue of the present invention may also contain other modifications, such as a tether between the C-terminus of the B chain and the N-terminus of the A chain as described more fully in U.S. Pat. No. 8,192,957.

A pharmaceutical composition may comprise such insulin analogues and which may optionally include zinc. Zinc ions may be included in such a composition at a level of a molar ratio of between 2.2 and 3.0 per hexamer of the insulin analogue. In such a formulation, the concentration of the insulin analogue would typically be between about 0.1 and about 3 mM; concentrations up to 3 mM may be used in the reservoir of an insulin pump. Modifications of meal-time insulin analogues may be formulated as described for (a) "regular" formulations of Humulin® (Eli Lilly and Co.), Humalog® (Eli Lilly and Co.), Novalin® (Novo-Nordisk), and Novalog® (Novo-Nordisk) and other rapid-acting insulin formulations currently approved for human use, (b) "NPH" formulations of the above and other insulin analogues, and (c) mixtures of such formulations.

Excipients may include glycerol, glycine, arginine, Tris, other buffers and salts, and anti-microbial preservatives such as phenol and meta-cresol; the latter preservatives are known to enhance the stability of the insulin hexamer. Such a pharmaceutical composition may be used to treat a patient having diabetes mellitus or other medical condition by administering a physiologically effective amount of the composition to the patient. The insulin analogues of the present invention may be formulated in the absence of zinc ions and in the presence of 5-10 mM ethylenediaminetetraacetic acid (EDTA) or ethyleneglycoltetraacetic acid (EGTA). The latter chelating agents are used in the absence of citrate ions.

A nucleic acid comprising a sequence that encodes a polypeptide encoding an insulin analogue containing a sequence encoding at least a B chain of insulin with an ortho-monofluoro-Phenylalanine at position B24 is also envisioned. This can be accomplished through the introduction of a stop codon (such as the amber codon, TAG) at position B24 in conjunction with a suppressor tRNA (an amber suppressor when an amber codon is used) and a corresponding tRNA synthetase, which incorporates a nonstandard amino acid into a polypeptide in response to the stop codon, as previously described (Furter, 1998, *Protein Sci.* 7:419-426; Xie et al., 2005, *Methods*. 36: 227-238). The particular sequence may depend on the preferred codon usage of a species in which the nucleic-acid sequence will be introduced. The nucleic acid may also encode other modifications of wild-type insulin. The nucleic-acid sequence may encode a modified A- or B-chain sequence containing an unrelated substitution or extension elsewhere in the polypeptide or modified proinsulin analogues. The nucleic acid may also be a portion of an expression vector, and that vector may be inserted into a host cell such as a prokaryotic host cell like an *E. coli* cell line, or a eukaryotic cell line such as *S. cereviciae* or *Pischia pastoris* strain or cell line.

For example, it is envisioned that synthetic genes may be synthesized to direct the expression of a B-chain polypeptide in yeast *Piscia pastoris* and other microorganisms. The nucleotide sequence of a B-chain polypeptide utilizing a stop codon at position B24 for the purpose of incorporating an ortho-monofluoro-Phenylalanine at that position may be either of the following or variants thereof:

```
(a) with Human Codon Preferences:
                                       (SEQ ID NO: 18)
TTTGTGAACCAACACCTGTGCGGCTCACACCTGGTGGAAGCTCTCTACCT

AGTGTGCGGGGAACGAGGCTAGTTCTACACACCCAAGACC (b) with Pichia Codon Preferences:
                                       (SEQ ID NO: 19)
TTTGTTAACCAACATTTGTGTGGTTCTCATTTGGTTGAAGCTTTGTACTT

GGTTTGTGGTGAAAGAGGTTAGTTTTACACTCCAAAGACT
```

Similarly, a full-length pro-insulin cDNA having human codon preferences and utilizing a stop codon at position B24 for the purpose of incorporating ortho-monofluoro-Phenylalanine at that position may have the sequence of SEQ ID NO: 20.

```
                                        (SEQ ID NO: 20)
    TTTGTGAACC AACACCTGTG CGGCTCACAC CTGGTGGAAG

CTCTCTACCT AGTGTGCGGG GAACGAGGCT AGTTCTACAC

ACCCAAGACC CGCCGGGAGG CAGAGGACCT GCAGGTGGGG

CAGGTGGAGC TGGGCGGCGG CCCTGGTGCA GGCAGCCTGC

AGCCCTTGGC CCTGGAGGGG TCCCTGCAGA AGCGTGGCAT

TGTGGAACAA TGCTGTACCA GCATCTGCTC CCTCTACCAG

CTGGAGAACT ACTGCAACTA G
```

Likewise, a full-length human pro-insulin cDNA utilizing a stop codon at position B24 for the purpose of incorporating an ortho-monofluoro-Phenylalanine at that position and having codons preferred by *P. pastoris* may have the sequence of SEQ ID NO: 21.

```
                                        (SEQ ID NO: 21)
    TTTGTTAACC AACATTTGTG TGGTTCTCAT TTGGTTGAAG

CTTTGTACTT GGTTTGTGGT GAAAGAGGTT AGTTTTACAC

TCCAAAGACT AGAAGAGAAG CTGAAGATTT GCAAGTTGGT

CAAGTTGAAT TGGGTGGTGG TCCAGGTGCT GGTTCTTTGC

AACCATTGGC TTTGGAAGGT TCTTTGCAAA AGAGAGGTAT

TGTTGAACAA TGTTGTACTT CTATTTGTTC TTTGTACCAA

TTGGAAAACT ACTGTAACTA A
```

Other variants of these sequences, encoding the same polypeptide sequence, are possible, given the synonyms in the genetic code.

Based upon the foregoing disclosure, it should now be apparent that insulin analogues provided will carry out the objects set forth hereinabove. Namely, these insulin analogues, when formulated under a broad range of protein concentrations from 0.6-3.0 mM (typically corresponding to strengths U-100 to U-500 in the cases of wild-type insulin and prandial insulin analogues), will exhibit enhanced rates of absorption from a subcutaneous depot and pharmacologic action in the regulation of blood glucose concentration while maintaining at least a fraction of the biological activity of wild-type insulin. Further, formulations whose rapid-acting pharmacokinetic and pharmacodynamic properties are maintained at concentrations of insulin analogue as high as 3.0 mM (U-500 strength) will provide enhanced utility in the safe and effective treatment of diabetes mellitus in the face of marked insulin resistance. It is, therefore, to be understood that any variations evident fall within the scope of the claimed invention and thus, the selection of specific component elements can be determined without departing from the spirit of the invention herein disclosed and described.

The following literature is cited to demonstrate that the testing and assay methods described herein would be understood by one of ordinary skill in the art.

Furter, R., 1998. Expansion of the genetic code: Site-directed p-fluoro-phenylalanine incorporation in *Escherichia coli*. *Protein Sci.* 7:419-426.

Merrifield, R. B., Vizioli, L. D., and Boman, H. G. 1982. Synthesis of the antibacterial peptide cecropin A (1-33). *Biochemistry* 21: 5020-5031.

Mirmira, R. G., and Tager, H. S. 1989. Role of the phenylalanine B24 side chain in directing insulin interaction with its receptor: Importance of main chain conformation. *J. Biol. Chem.* 264: 6349-6354.

Sosnick, T. R., Fang, X., and Shelton, V. M. 2000. Application of circular dichroism to study RNA folding transitions. *Methods Enzymol.* 317: 393-409.

Wang, Z. X. 1995. An exact mathematical expression for describing competitive biding of two different ligands to a protein molecule *FEBS Lett.* 360: 111-114.

Weiss, M. A., Hua, Q. X., Jia, W., Chu, Y. C., Wang, R. Y., and Katsoyannis, P. G. 2000. Hierarchiacal protein "undesign": insulin's intrachain disulfide bridge tethers a recognition α-helix. *Biochemistry* 39: 15429-15440.

Whittaker, J., and Whittaker, L. 2005. Characterization of the functional insulin binding epitopes of the full length insulin receptor. *J. Biol. Chem.* 280: 20932-20936.

Xie, J. and Schultz, P. G. 2005. An expanding genetic code. *Methods*. 36: 227-238.

What is claimed is:

1. A pharmaceutical formulation comprising insulin, wherein the insulin B-chain polypeptide comprises an ortho-monofluoro-Phenylalanine substitution at position B24 in relation to the sequence of human insulin, in combination with a substitution of Aspartic Acid at position B10 in relation to the sequence of human insulin, a substitution of Glutamic Acid at position B29 in relation to the sequence of human insulin, and a substitution of Glutamic Acid at position A8 in relation to the sequence of human insulin, wherein the insulin is present at a concentration of between 0.6 mM and 3.0 mM.

2. The pharmaceutical formulation of claim 1, wherein the insulin is present at a concentration of at least 2 mM.

3. The pharmaceutical formulation of claim 1, wherein the B chain polypeptide additionally contains a substitution at position B28 in relation to the sequence of human insulin selected from the group consisting of Aspartic Acid and Lysine.

4. The pharmaceutical formulation of claim 1, wherein the B-chain polypeptide also contains a Lysine substitution at position B3 in relation to the sequence of human insulin.

5. The pharmaceutical formulation of claim 4, wherein the B chain polypeptide comprises SEQ ID NO: 8, wherein the Xaa at residue 10 is Asp.

6. The pharmaceutical formulation of claim 1, wherein an A-chain polypeptide sequence has the amino acid sequence of SEQ ID NO: 9, wherein the Xaa at residue 8 is Glu.

7. A polypeptide comprising the insulin B-chain polypeptide sequence containing an ortho-monofluoro-Phenylalanine substitution at position B24 in relation to the sequence of human insulin, in combination with: a substitution of Aspartic Acid at position B10 in relation to the sequence of human insulin, a substitution of Glutamic Acid at position B29 in relation to the sequence of human insulin, and a substitution of Glutamic Acid at position A8 in relation to the sequence of human insulin.

8. The polypeptide of claim 7, wherein the polypeptide is a proinsulin analogue or single-chain insulin analogue.

9. The polypeptide of claim 7, wherein the polypeptide additionally contains a Lysine substitution at position B3 in relation to the sequence of human insulin.

10. A method of lowering the blood sugar level of a patient, the method comprising administering the pharmaceutical formulation of claim 1 to said patient.

11. The method of claim 10, wherein the insulin is present in the formulation at a concentration of at least 2 mM.

* * * * *